(12) United States Patent
Albertsen et al.

(10) Patent No.: US 6,265,640 B1
(45) Date of Patent: *Jul. 24, 2001

(54) NUCLEOTIDE SEQUENCES MEDIATING FERTILITY AND METHOD OF USING SAME

(75) Inventors: Marc C. Albertsen, West Des Moines; Larry R. Beach, Des Moines; John Howard, Des Moines; Gary A. Huffman, Des Moines, all of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/211,416

(22) Filed: Dec. 10, 1998

Related U.S. Application Data

(63) Continuation of application No. 08/485,845, filed on Jun. 7, 1995, now Pat. No. 5,850,014, which is a continuation of application No. 08/103,739, filed on Aug. 2, 1993, now Pat. No. 5,478,369, which is a continuation-in-part of application No. 07/537,183, filed on Jun. 12, 1990, now abandoned, which is a continuation-in-part of application No. 08/171,302, filed on Dec. 21, 1993, now abandoned, which is a continuation of application No. 07/848,433, filed on Mar. 9, 1992, now Pat. No. 5,432,068.

(51) Int. Cl.⁷ .............................. A01H 5/00; A01H 4/00; C12N 5/04
(52) U.S. Cl. ..................... 800/303; 800/298; 800/275; 800/271; 536/24.71; 536/23.7
(58) Field of Search ................................. 800/298, 275, 800/271, 303; 536/24.71, 23.7

(56) References Cited

U.S. PATENT DOCUMENTS 5,850,014 * 12/1998 Albertsen et al. ................... 800/298

* cited by examiner

Primary Examiner—Gary Benzion
(74) Attorney, Agent, or Firm—Patricia A. Sweeney

(57) ABSTRACT

Fertility in a plant is controlled by inactivating a gene critical to fertility, and inserting into the plant the criticial gene linked to an inducible promoter.

4 Claims, 14 Drawing Sheets

```
         A  L  A  L  A  L  L  V  A  V  A  D  P  F  G  L
HN92 742 #2  GCCCTGGCCCTGGCCCTGGCCCCTCCTAGTCGCGGTCGGCCGACCCGTTCGGCCTC
             |||||||||||||||||||||||||       ||||||||||||||||||||||||
MS45         GCCCTGGCCCTGGCCCTGGCCCTCCCTA    GTCGGCGACCCGTTCGGCCTC
             A  L  A  L  A  L  L           V  A  D  P  F  G  L
```

Fig. 7

PETUNIA
DOMINANT STERILITY
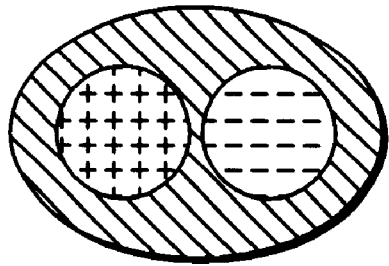
100% STERILE POLLEN
MAIZE
RECESSIVE STERILITY
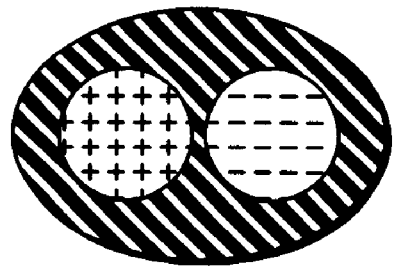
100% FERTILE POLLEN
Fig. 9

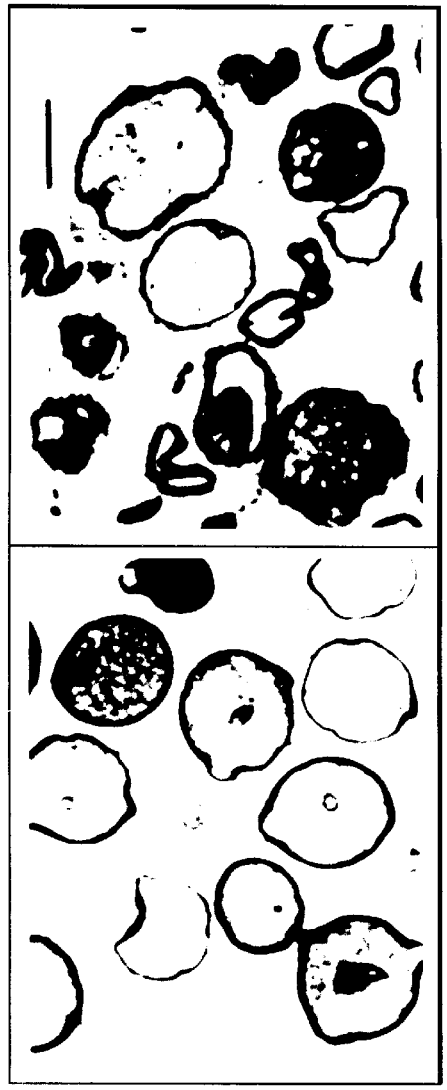
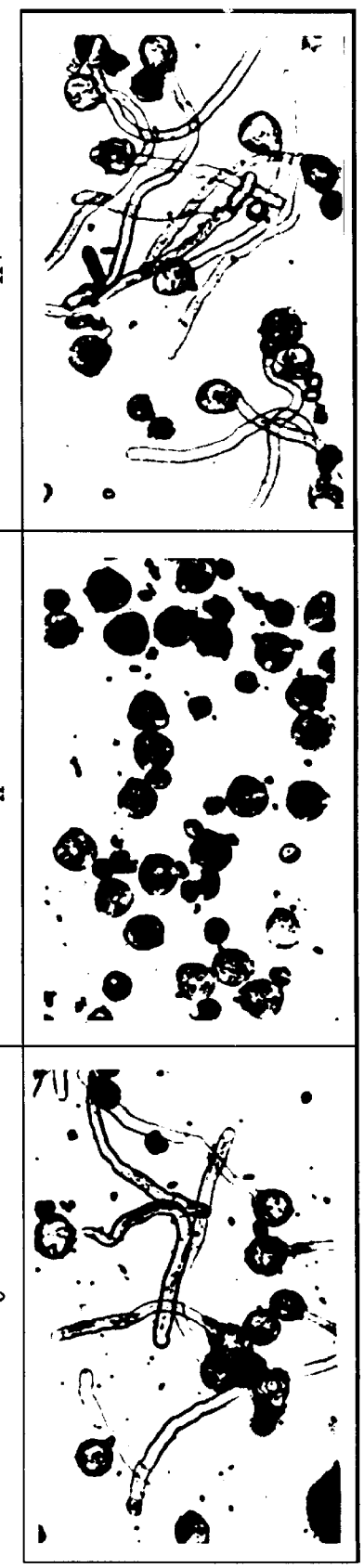
FIG. 11D
FIG. 12A FIG 12B FIG. 12C

NUCLEOTIDE SEQUENCES MEDIATING FERTILITY AND METHOD OF USING SAME

REFERENCE TO PRIOR APPLICATION

This application is a continuation of previously filed and application Ser. No. 08/485,845, filed Jun. 7, 1995 now U.S. Pat. No. 5,850,014, which is a continuation-in-part of previously filed and U.S. application Ser. No. 08/171,302 filed Dec. 21, 1993 now abandoned, which is a continuation of U.S. application Ser. No. 07/848,433 filed Mar. 9, 1992 now U.S. Pat. No. 5,432,068, and this application is also a continuation of U.S. application Ser. No. 08/103,739 filed Aug. 2, 1993 now U.S. Pat. No. 5,478,369, both of which application Ser. Nos. 07/848,433 and 08/103,739 are a continuation-in-part of U.S. application Ser. No. 07/537,183, filed Jun. 12, 1990 now abandoned.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

In Brassica, the plant is normally self sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Maize plants (*Zea mays* L.) present a unique situation in that they can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

A reliable method of controlling male fertility in plants would offer the opportunity for improved plant breeding. This is especially true for development of maize hybrids, which relies upon some sort of male sterility system.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

Hybrid maize seed is typically produced by a male sterility system incorporating hand manual detasseling. To produce hybrid seed, the male tassel is removed from the growing female inbred parent, which has been planted in alternating rows with the other male inbred parent. Providing that there is sufficient isolation from sources of foreign maize pollen, the ears of the female inbred will be fertilized only with pollen from the male inbred. The resulting seed is therefore hybrid and will form hybrid plants. What is sought is an efficient, inexpensive, reliable method of rendering the female plant male sterile. Current methods have considerable disadvantages, as outlined below. This invention addresses those disadvantages.

Further, it can be appreciated that control of female fertility has advantages. Currently, once the female inbred is rendered male sterile, and the cross pollination has occurred, the male inbred plant is then physically removed since any inbred seed on the plant cannot be sold and should not be released. This adds to the expense through the removal process. However, if the male inbred could be rendered female infertile, it would not be necessary to remove the rows of males, and any chance of inbred seed becoming available is reduced. Approximately 20 percent of acerage in developing an inbred must be devoted to growing the male inbred. With female sterility in the male inbred, the male and female inbred can be grown together, with considerable cost savings. Unfortunately, the hand manual detaseling process is not entirely reliable. Occasionally a female plant will be blown over by a storm and escape detasseling. The natural variation in plant development can also result in plants tasseling after manual detasseling is completed. Or, a detasseler will not completely remove the tassel of the plant. In any event, the female plant will successfully shed pollen and some female plants will be self-pollinated. This will result in seed of the female inbred being harvested along with the hybrid seed which is normally produced.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and the eliminate self-pollination in the production of hybrid seed.

The laborious detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown and to insure diversity.

There can be other drawbacks to CMS. One is an historically observed association of a specific variant of CMS with susceptibility to certain crop diseases. This problem has led to virtual abandonment of use of that CMS variant in producing hybrid maize.

Another form of sterility, genic male sterility, is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes and make use of the system convenient. Patterson also described a genic system of chromosomal translocations which are effective, but complicated. U.S. Pat. Nos. 3,861,709 and 3,710,511.

Many other attempts have been made to improve on these drawbacks. For example, Fabijanski, et al., developed several methods of causing male sterility in plants (see EPO 89/3010153.8 publication no. 329,308 and PCT application PCT/CA90/00037 published as WO 90/08828). One method includes delivering into the plant a gene encoding a cytotoxic substance associated with a male tissue specific promoter. Another involves an antisense system in which a gene critical to fertility is identified and an antisense to the gene inserted in the plant. Mariani, et al. also shows several cytotoxin encoding gene sequences, along with male tissue specific promoters and mentions an antisense system. See EP 89/401,194. Still other systems use "repressor" genes which inhibit the expression of another gene critical to male sterility. PCT/GB90/00102, published as WO 90/08829.

As noted, an essential aspect of much of the work underway with male sterility systems is the identification of genes impacting male fertility.

Such a gene can be used in a variety of systems to control male fertility. Previously, a male sterility gene has been identified in *Arabidopis thaliana* and used to produce a male sterile plant. Aarts, et al., "Transposon Tagging of a Male Sterility Gene in Arabidopsis", Nature, 363:715–717 (Jun. 24, 1993). Such genes to date are mutants which cause the plant to be sterile.

The disadvantage of such prior systems is that the plant is normally fertile and sterility is initiated by a variety of approaches such as mutant gene, tissue specific cell killing, spraying a chemical that induces sterility or the like, and are complex, difficult to use, require some detasseling, are not reliable in causing all the desired plants to be male sterile, thereby allowing some inbred seed to be produced and at times use considerable amounts of chemicals or DNA sequences undesirable in a grain producing plant. They all cause sterility and fertility is restored by reversion to the native constitutively fertile state.

Here, the inventors have taken an entirely different approach. The invention allows the plant to be constitutively sterile, with fertility (not sterility) induced. This has several advantages.

First, inducement of sterility is inefficient. There are in excess of six to fourteen million pollen grains in one tassel. The inducement of sterility thus must be extremely foolproof to avoid unintentional self pollination. On the other hand, inducement of fertility need only be minimally effective since more than adequate pollen will be produced through partial restoration to achieve fertilization and increase in parent seed. Chemical treatment failure results in under production of pollen, and since pollen is normally overproduced by a wide margin, the process of this invention for production of parent seed will tolerate a treatment failure rate as high as 70% to 80% with minimal effects on yield of parent seed.

Second, there is no detasseling required, whereas with CMS, there is only a reduction of detasseling.

Third, by having the critical gene normally "off", chemical treatment is not necessary in the large-scale production of hybrid seed, so that chemical usage (and associated expense) is minimized and the risk of treatment failure is present only in the carefully controlled, limited scale production of parent seed, where self-pollination is desired.

Thus, one objective of the invention is a unique variation to the method of controlling sterility by using the DNA molecule to cause a plant to be sterile after transformation, with fertility, not sterility, induced.

An object of the invention is to provide a nucleic acid sequence, the expression of which is critical to male fertility in plants.

Another object of the invention is to provide a DNA molecule encoding an amino acid sequence, the expression of which is critical to male fertility in plants.

A further object of the invention is to provide a method of using such DNA molecules to mediate male fertility in plants.

A still further object is to provide a method of mediating fertility in plants by regulating expression of the DNA molecule naturally occurring in the plant.

Yet another object is to provide a method of mediating fertility in plants by delivering the DNA molecule into a plant such that expression of the DNA molecule may be controlled.

Another object is to provide plants wherein fertility of the plants is mediated by the DNA molecule.

A further object is to use plants having fertility mediated by the DNA molecules in a plant breeding system.

Further objects of the invention will become apparent in the description and claims that follow.

SUMMARY OF THE INVENTION

This invention relates to control of plant fertility by providing a constitutively sterile plant, wherein fertility may be induced. Plants are rendered controllably sterile by using an inducible promoter to regulate expression of the DNA molecule such that the gene is normally "off" and the plant is thus sterile. When the promoter is induced, the plant becomes fertile.

BRIEF DESCRIPTION OF THE DRAWINGS

FIG. 7 (SEQ ID NOs: 3–6, respectively)shows the nucleotide and amino acid sequence of fertile revertant plant DNA after Ac transposition.

FIG. 9 is a schematic representation of sporophytic influence (diagonal lines) on the developing microspores in chalcone synthase (CHS) heterozygous plants. The lack of CHS function in the sporophyte is indicated by a white background (FIG. 9A) and the presence of CHS function is represented by a black background (FIG. 9B).

FIG. 11 is photographic representations of cross sections of developmentally identical anthers from inbred petunia line V26 (left column) and from CHS-deficient plant 025425.1 (right column), which had been harvested, fixed, embedded, transversely sectioned and stained with toluidine blue as described in Example 3. FIG. 11D shows mature pollen at dehiscence. In FIG. 11, P represents pollen; E, endothecium; S, stomium; and C, cuticle.

FIG. 12 is a photographic representation of the restoration of pollen germination and tube growth to petunia CHS-deficient pollen by the fertility restoring flavonol, kaempferol. Pollen was collected from conditionally male fertile anthers, suspended in germinating medium, and kaempferol (K+, FIG. 12C) or DMSO (K−,FIG. 12B) added to 1 $\mu$M final concentration. Representative fields of pollen are pictured after 4 hours of incubation. The germination and tube growth observed in the kaempferol rescued CMF pollen (FIG. 12C) is indistinguishable from the wild type V26 control (C, FIG. 12A) which received DMSO only. The non-supplemented CMF pollen (FIG. 12B) shows swelling at the germination pore in some grains but no pollen tubes are extruded.

DISCLOSURE OF THE INVENTION

Figure 1:
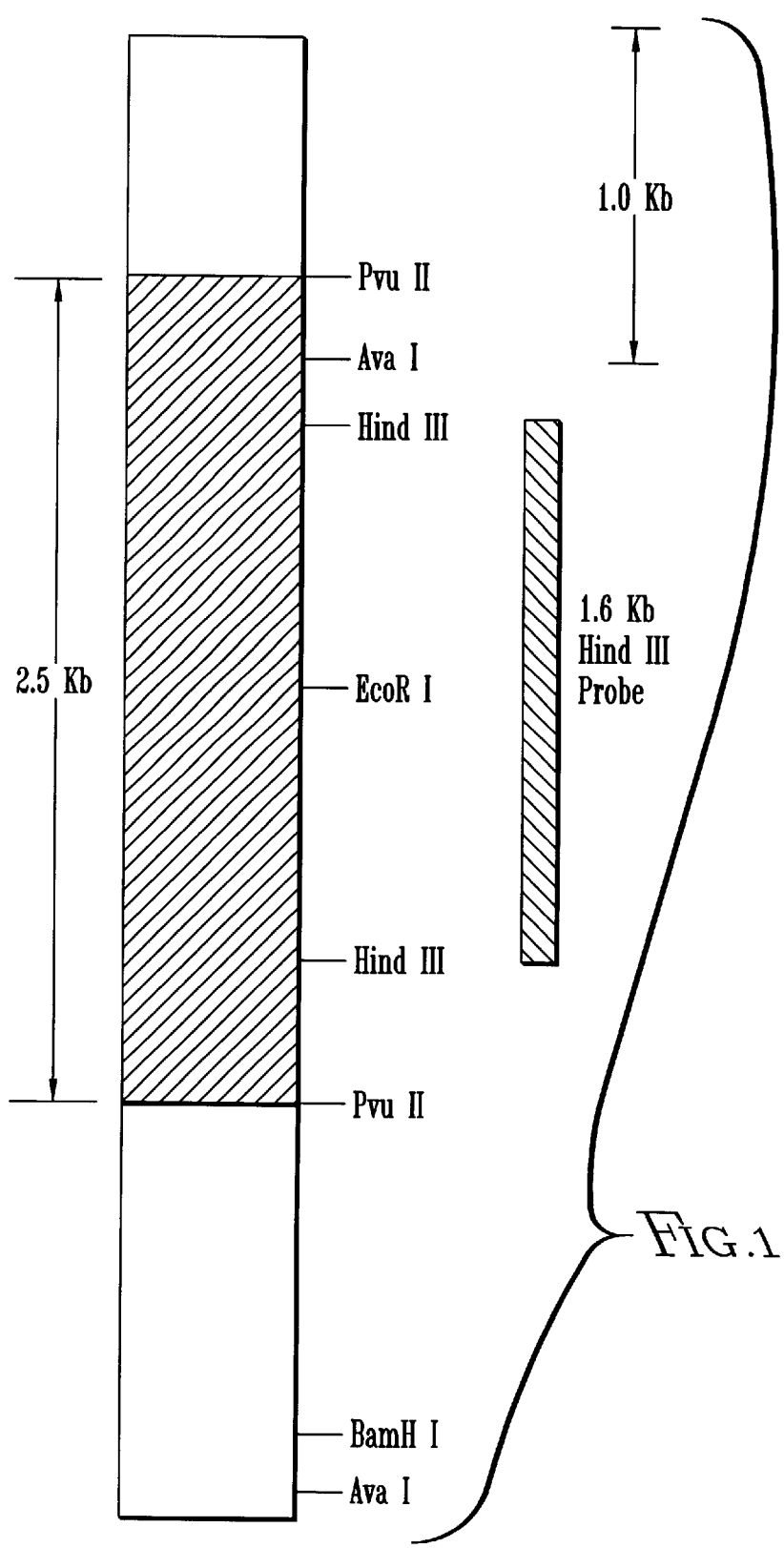
FIG. 1 is a restriction map of the transposon Ac.

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

This invention differs from conventional approaches to sterility in plant breeding and seed production in that an inducible promoter is used to regulate expression of the gene which is known to be critical to plant male fertility. The first step in the practice of this invention is therefore the selection of a gene on which fertility is dependent. One type are the male fertility MS45 DNA molecules described below. Also described are genes impacting flavonone production critical to male fertility.

The selected gene is cloned, the plant native gene inactivated and the modified gene is inserted into an expression sequence with an inducible promoter responsive to external control.

Using transformation and gene substitution, the gene is inactivated in the genome of the plant and replaced by the genetically-engineered gene incorporated into the expression sequence with the inducible promoter.

This invention is unique in that the process results in using the inducible promoter to induce fertility, not sterility. In this invention, the selected gene's promoter sequences are removed so that the gene is not transcribed and the plant is sterile. When it is desired to increase the sterile plant, fertility is restored by inducing expression of the critical gene. In the preferred embodiment this is accomplished by treating growing sterile plants with a specific non-phytotoxic chemical.

In general, in accordance with the invention described herein, the DNA molecule herein described is incorporated into the plant along with a necessary promoter which is inducible. The plant will be sterile since the DNA molecule is not expressed and when the promoter is induced, the plant will be fertile. The native gene producing the DNA molecule product is in normally fertile plant may be inactivated by any of a variety of methods described below, such as backcrossing or homologous recombination.

The following is presented to illustrate the invention and is not intended to limit its scope.

FERTILITY DNA MOLECULES

Identifying Genes Critical to Male Fertility

Genetic male sterility results from impacting one of the genes responsible for a specific step in microsporogenesis, the term applied to the entire process of pollen formation. These genes can be collectively referred to as male fertility genes. There are many steps in the overall pathway where a mutation can lead to male sterility. This seems aptly supported by the frequency of genetic male sterility in maize. New alleles of male sterility mutants are uncovered in materials that range from elite inbreds to unadapted populations.

The procedures for identifying and cloning a male sterile gene are the same as those known in the art to be utilized to clone other genes. The preferred method is transposon (transposable element) tagging because most instances of genetic male sterility in maize are the result of recessive gene mutations. Cloning techniques that require knowledge of the protein sequences of a male sterile gene translation product cannot be used at present because a common gene product of male sterile genes is not yet known.

The procedure for tagging maize genes with transposable elements is known, as reviewed by H. P. Doring, "Tagging Genes With Maize Transposable Elements. An Overview," Maydica 34 (1989): 73–88, and described in U.S. Pat. No. 4,732,856 to Federoff ("Transposable Elements and Process for Using Same"), the disclosures of which are, as previously noted, incorporated herein in their entirety.

One of the methods by which this is carried out is by inter-crossing a maize strain carrying active transposable elements and a dominant allele of the target gene involved in microsporogenesis with a normal maize strain that does not carry transposable elements. Specific gene tagging efficiency can be and preferably is enhanced by positioning the transposable element in the proximity of the target gene locus. Progeny from the inter-crosses are selfed and subsequently screened for the most useful mutations. The preferred phenotypes are plants which do not extrude anthers and those which do not produce pollen. Most preferred are phenotypes which do not extrude anthers because this phenotype can easily be screened visually prior to pollination time by gross observation. These male sterile plants represent putative instances in which a transposable element has excised from its original location and has transposed to a locus bearing a gene which is essential for pollen development. Once the transposable element has transposed to such a locus, the gene is inactivated. It will then behave as a recessive gene and result in male sterility. These mutant plants can be crossed to tester stocks for the transposable element to confirm that the element is still present.

Once it has been confirmed that the desired transposable element has transposed into the target gene, genomic clones which hybridize to the transposable element are constructed. The element adjacent sequences of the clones are then used as probes in Southern hybridizations with genomic DNA from strains carrying the mutant allele, the revertant allele, and the wild-type allele. The RDNA which reveals the expected differences in size (reflecting the presence or absence of the transposable element) carries the desired modified target gene.

In practice, the frequency with which a particular locus can be targeted with a transposable element usually varies from $10^{-5}$ to $10^{-6}$. However, 100,000 maize plants can easily be grown on an area of less than 10 acres. In addition, under certain circumstances the frequency of the element-induced mutations can be increased. For example, the particular transposable element to be used for gene tagging can be linked to the gene to be tagged by the element. For two different transposable element systems, Ac and SpmIEn, the transpositions of these elements occurs preferentially to sites on the chromosome where the element was located before the transposition. Alternatively, different transposable elements have different frequencies of mutation induction. For example, the transposable element called Mutator (Mu) is able to induce new mutations at a frequency 30 to 50 times higher than the frequency in control plants. Additionally, the rate of mutation induction can be influenced by the sex of the element carrying parent. While it cannot be predicted which of the reciprocal crosses will give the higher mutation rate, transposon tagging can readily be performed.

At least seven different maize transposable elements have been cloned at this time. These are Ac, Spm/En, Mu, Tz86, Bs1, rDt, and Mpi1. Any of these can be used to clone genes in which a transposable element resides.

One skilled in the art will appreciate this is but one example of means to locate such genes and that other methods are well known.

One collection of mutant genes is already known, and has been described by Albertsen, et al. "Developmental Cytology Genetic Male Sterile Loci in Maize". Can. J. Genet. Cytol. 23: 195–208, (1981), as noted, incorporated herein by reference. These are known as male-sterile (ms) genes. These genes affect development of the pollen only; they have no effect on female organ development. These genes disrupt microsporogenesis at characteristic stages of pollen development, rendering the plant male sterile.

Once the mutant gene from any of the foregoing sources has been cloned, it is used as a probe to clone the wild type allele. This is possible because the mutated gene is very closely similar to the wild type allele, and as such, hybridizes to the wild type allele. Once the normal gene has been identified and cloned, the region of the gene known as a promoter region is identified. This region is involved in the start of transcription of that gene.

Genes which are essential to pollen development can also be identified without intermediate use of mutations by isolating mRNA's that are uniquely present during pollen development and constructing a CDNA that can be used to probe a genomic library for the corresponding gene.

EXAMPLE 1

MS45 Male Fertility Gene

Tagging

Ac (Activator) is a well known transposable element first characterized in 1954 by Barbara McClintock, (McClintock, B., *Cold Spring Harbor Symp. Quant. Biol.* 21:197–216 (1956); McClintock, B., *Camegie Inst. Wash. Yrbook,* 53:254–260 (1954); see also Federoff, U.S. Pat. No. 4,732,856 issued Mar. 22, 1988 and Dooner, U.S. Pat. No. 5,013,658 issued May 8, 1991). Ac was used to clone MS45. A restriction map of Ac used here is depicted in FIG. 1. Those skilled in the art are familiar with the restriction sites of Ac. In sum, The Ac transposon went from the P-vv locus on chromosome 1 to chromosome 9. The only currently described male sterility gene on chromosome 9 is ms2, which has never been cloned or sequenced. See Albertsen, M. and Phillips, R. L, "Developmental cytology of 13 genetic male sterile loci in maize" *Canadian Jnl. of Genetics and Cytology* 23:195–208 (January 1981). The only cloned fertility gene is the Arabidoosis gene described. Aarts, et al., supra. Test cross progeny have confirmed the MS2 and MS45 are not allelic.

Plant Materials

Three maize lines were used, all of which are widely available to maize geneticists and regularly used by those skilled in the art and are described at Chen, et al., "Transposition of Ac from the P locus of maize into unreplicated chromosomal sites" *Genetics* 117:109–116 (September 1987). Such lines may be obtained, for example, from the authors of the above article, from Pioneer Hi-Bred International, Inc., or any one of many public sources such as the Maize Genetics Stock Cooperation Center, University of Illinois, Urbana/Champagne, Department of Agronomy S-123 Turner Hall, 1102 South Goodwin Avenue, Urbana, Ill., 61801.

The first line is W23P-vv. The P-vv allele is caused by the insertion of the mobile element Ac into the P locus. Emerson, R. "The inheritance of a recurring somatic variation in variegated ears of maize" *Am. Nat* 48:87–115 (1914); Brink, R. and Nilan, R. "The relation between light variegated and medium variegated pericarp in maize" *Genetics* 37:519–544 (1952) and Barday, P. and Brink, R. "The relation between modulator and Activator in maize" *Proc. Nat'l. Acad. Sci. USA* 40:1118–1126 (1954). The P gene is a maize gene well characterized and fully detailed in the art. The P gene induces pigmentation of the pericarp in maize. Flavanone is reduced to phlobaphenes which cause pigmentation of the pericarp. One example of the detailed information on the P gene which is available to one skilled in the art is the discussion by Lechelt, et al., "Isolation and molecular analysis of the maize P locus," *Mol. Gen. Genet.* 219:225–234 (1989) and Chen, et al., "Molecular Analysis of Ac transposition and DNA replication" *Genetics*. This is an excellent marker gene because of its function in regulating the color of pericarp. Red stripes form to show the excision of Ac from P, restoring gene function and providing red pericarp.

The P-gene (P-vv) is on the same chromosome as known genetic male steriles previously mapped to chromosome 1. It has been shown that Ac transposes on the same chromosome 67% of the time. Van Schaik, N. V. and Brink, R. A., "Transpositions of modulator, a component of the variegate pericarp allele in maize" *Genetics* 44:725–738 (1959). However, this did not occur here, as the Ac transposed to chromosome 9. P-w itself greatly facilitates transposon tagging because it is possible to visually observe when Ac has transposed from the P-gene and is elsewhere in the genome.

4C063 is a white inbred line that combines well with W23P-vv to give good hybrid plants with easily scored kernels. W22r-sc:m3 is a line with the Ds element at the R-locus. The plant is genetically dominant at all the anthocyanin pathway genes (A1, A2, Bz1, Bz2, Cl, C2, Pr, R).

Because Ds causes R to become dysfunctional, no anthocyanin are produced in the kernel.

This was coupled with use of W22r-sc:m3 stocks, in which Ds is integrated into the R-gene. The Ds element responds to the presence of Ac, by transposing to another site on the genome. It is, in fact, a defective Ac. The Ac transposon can move in and out of a gene on its own, whereas Ds cannot move unless Ac is present somewhere on the genome. The R gene is a gene in maize studied in considerable depth. It is known to encode enzymes required for synthesis of anthocyanin pigments. An example of the detailed information known regarding the R gene is the description and sequencing information found at Dellaporta, et al., Stadler *Symposium* 18:263 (1988) and Ludwig, et al., "Lc a member of the maize R gene family responsible for tissue-specific anthocyanin production, encodes a protein similar to transcriptional activators and contains the mv-homology region", *Proc. Nat. Acad. Sci.* 86:7092–7096 (September 1989) and use of the gene as a visual marker, described at Bowen, et al., "R Genes as visual markers for corn transformation" Abstract edit. Gallagher, Academic Press (October 1989) and Ludwig, et al., "A regulatory gene as a novel visible marker for maize transformation" *Science* 247: 449–450 (January 26, 1990).

In the W22 r-sc:m3 stock, all kernel anthocyanin genes are dominant. The kernel color is yellow, however, because of Ds interrupting function of the R-gene. In the presence of Ac, however, the Ds element can transpose, resulting in purple-spotted kernels. Therefore, it was possible to 1) visually determine when Ac transposed away from the P-gene (red-striped or full red pericarp) and 2) determine whether Ac was still active (purple spots in the aleurone). By selecting either all red kernels or kernels with red pericarp stripes over the embryo that also have purple spots in the aleurone, it was possible to greatly enrich for those cases where an active Ac has transposed to another location in the genome. By selfing plants resulting from these kernels, one can screen progeny families for any mutations affecting tassel or anther development. In this case, selfed families for the segregation of male-sterile plants were created.

Co-Segregation Analysis

Conducting co-segregation analysis for specific gene tagging and cloning strictly through a molecular approach can be tedious and time-consuming. The ACsystem, however, is well suited to co-segregation analysis at the field genetics level. Interaction between active Ac and Ds at the R-gene (r-sc:m3) can be utilized. Plants crossed with Ac were selfed and grown and those families segregating for male sterility identified. Once a family was identified that segregated for male sterility, additional seed was planted to cross with r-sc:m3 for co-segregation analysis. Each plant (fertiles and steriles) was crossed with r-sc:m3, the kernel color segregation observed on each ear and correlated with whether the plants were male fertile or male sterile.

A family was observed where the plants were mostly male sterile, with a few extruded abnormal anthers scattered about the tassel. In most cases, these abnormal anthers did not have pollen present. When every plant from this family was crossed with r-sc:m3, co-segregation of Ac with the male-sterile phenotype was observed as set forth in the table below.

TABLE 1

Segregation of trhn-90-40 crossed with r:m3

| Plant Phenotype | Ear Phenotype | Observed Number | Expected Number |
| --- | --- | --- | --- |
| Sterile | all kernels purple spotted | 8 | 8.25 |
| Fertile | ½kernels purple spotted 1/2 kernels no spots | 16 | 16.50 |
| Fertile | all kernels no spot | 9 | 8.25 |

Male-sterile plants always produced ears with every kernel purple spotted. Two thirds of the fertile plants had ears that segregated 50% spotted kernels and 50% yellow kernels. One third of the fertiles produced ears with all yellow kernels. This showed Ac had transposed into a gene responsible for male fertility and interrupted its function. The gene acts as a recessive, and when homozygous, results in male sterility. This segregation was verified in further plantings.

Molecular Analysis

Southern analysis was carried out to confirm association of Ac with sterility. Southern analysis is a well known technique to those skilled in the art. This common procedure involves isolating the plant DNA, cutting with restriction endonucleases and fractionating the cut DNA on an agarose gel and transferring to nitrocellulose membranes to separate the DNA by molecular weight. It was then hybridized with the probe fragment which was radioactively labeled with P32 and washed in an SDS solution. Southern, E., "Detection of a specific sequences among DNA fragments by gel electrophoresis," *J. Mol. Biol.* 98:503–517 (1975).

DNA was isolated from sterile-crossed progeny and fertile-crossed progeny, keeping the purple-spotted kernel seedlings separate from the yellow kernel seedlings. DNA was isolated from the top two leaves of one month old plants using an Urea procedure as described at Dellaporta, et al., "A plant DNA minipreparation: version II" *Plant Mol. Bio. Rep.* 1:19–21 (1983). The isolated DNA was cut with PvuII in order to find a 2.5 kb fragment only associated with Ac as shown in the restriction map (FIG. 1). Approximately 8 ug of DNA was digested with the appropriate enzyme according to the manufacturer's instructions (Promega). DNA digests were electrophoresed through a 0.75% Sea Kem GTG agarose gel and transferred to Duralon-UV nylon membrane by capillary bloffing and fixed to the membrane by baking 1 hour at 85 C. The 1.6 kb HindluI fragment of Ac was used as a probe in the Southern Blot analysis.

Figure 2:
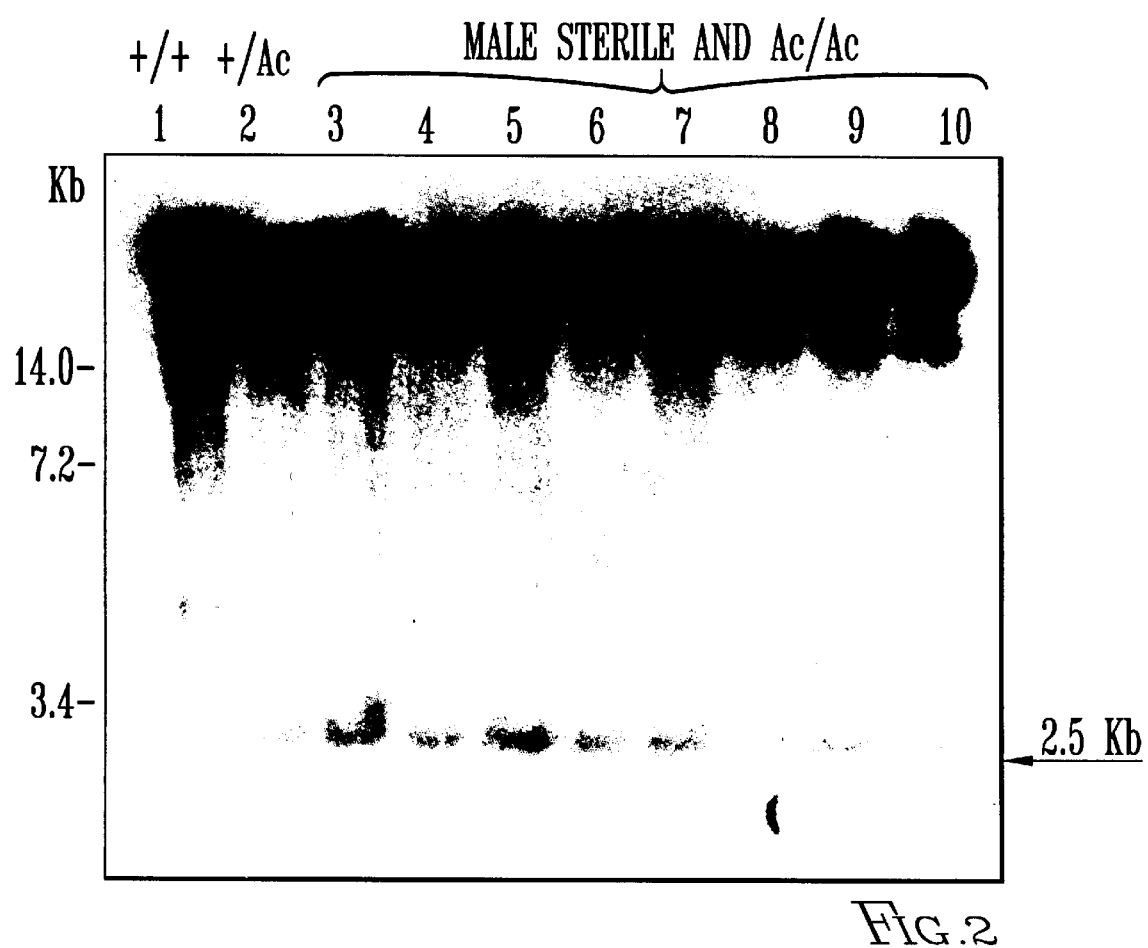
FIG. 2 is a gel of a Southern Blot analysis of Pvull digested DNA from an Ac family segregating for sterility and hybridized with an internal 1.6 kb Hindull from Ac.

The results are shown in the gel at FIG. 2. At FIG. 2, the male steriles are lanes 3–10. Lane 2 is the heterozygous fertile plant and lane 1 the wild type. As this gel confirms, a 2.5 kb fragment band appeared in all sterile (purple spotted kernels) plants and did not appear in any of the fertile (yellow kernels) plants. This confirms the Ac was either closely linked to the male fertility locus or inserted into the locus, inhibiting the function of the gene and resulting in a male sterile phenotype.

Cloning

The DNA adjacent to the known Ac sequence was cloned and used in obtaining the entire gene.

To summarize, the male fertile plant DNA and the male-sterile plant DNA were digested with restriction endonucleases Pst I, Eag I, Sal I, Sac I, and Xba I to locate a single band with the Ac element. Fragments were electrophoresed, Southern transferred, and hybridized with the Ac HindliI fragment. A 6 kb PstI fragment was identified that co-segregated with male-st element. The inverse PCR method of Baker et al was used to isolate the DNA associated with Ac. Earp, D. J. Lowe, B. and Baker B., "Amplification of genomic sequences flaking transposable elements in host and heterologous plants: a tool for transposon tagging and genomic characterization," *Nucleic Acids Research* 18:3271–3279 (1990).

Figure 3:
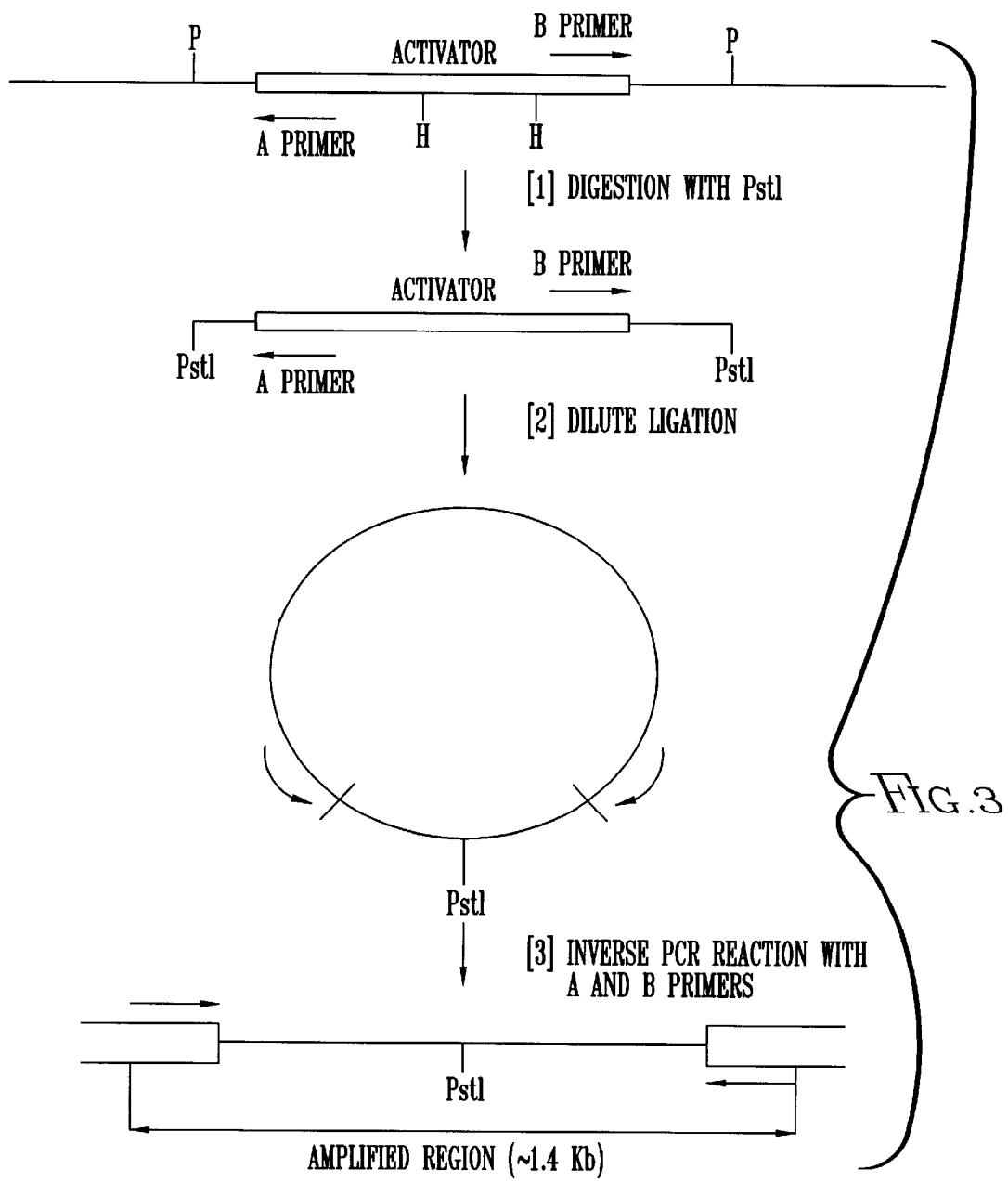
FIG. 3 is a schematic representation of inverse polymerase chain reaction.

A schematic depicting the well known inverse polymerase chain reaction procedure is shown in FIG. 3. After obtaining the 6 kb fragment, the ends were relegated. A and B primers were identified readily since the sequence of Ac is known. Thus the 5' and 3' oligonucleotides could be identified, and, according to the inverse PCR technique, react to amplify the intervening sequences. The A and B primers were run from each side of the religated circle where the Ac had been. In this way, the DNA between the ends of the Ac was amplified and a 1.3 kb segment of DNA isolated. The known 4.8 kb Ac fragment plus the amplified 1.3 kb IPCR product nearly equaled the 6.0 kb Pst I fragment isolated previously.

Details of this above summarized procedure are as follows. Genomic DNA was isolated as described above. 20 ug of DNA was digested with 20 units of PstI according to the manufacturer's instructions (Promega). The digested DNA was electrophoresed as described above using a preparative comb. A gel fragment, which contained DNA with a molecular weight between 5.5 and 6.5 kilobases, was excised from the gel. The DNA was electro-eluted from the agarose by using Spectra/Por membrane #2, MWCO 12-14000 (Spectrum Medical Industries, Inc.) which contained 0.4 ml sterile water and electrophoresing against 1×Tris-Acetate buffer pH 8.0 (TAE). The isolated DNA was extracted consecutively with Tris-equilibrated phenol pH 7.0:chloroform (1.1), chloroform, then ethanol precipitated, dried and re-suspended in sterile water. Ligations were performed according to the manufacturers instructions (Bethesda Research Laboratories) using the Psi digested genomic DNA at a final concentration of 20 ng/u. Ligations were done 18 hours at 14 C.

Oligonucleotide primers were synthesized on an Applied Biosystems model 394 DNA/RNA synthesizer. Primer B5 (SEQ ID NO: 8) was essentially the same as described by Earp et al., supra, except for an EcoRI site engineered at the 5' end and an extra two bases at 3' end. The sequence of both primers used in the Ac inverse PCR reaction are as follows:

A5: 5' GATAGMTTCGGTACGGGATTTTCCCATC-CTACTT 3'

B5: 5' GGTAGMTTCGTITICGTTTCCGTCCCG-CAAGTT 3

PCR was carried out using 25 ng of circularized genomic template DNA in a reaction containing 2 uM of each primer, 0.24 mM of each dNTP, 3 units of Hot Tub polymerase (Amersham) in a 1× reaction buffer supplied by the manufacturer. Amplification was performed in a MJ Research Inc. model PTC-100-96 thermocycler under the same conditions as described by Earp et al., supra. Reaction products were electrophoresed on 1% LMP agarose gels (Bethesda Research Laboratories). The amplification product was isolated from the gel using a Magic PCR kit (Promega) and re-amplified using the above conditions.

cDNA Isolation cDNA library screenings are commonly known among those skilled in the art, and are described at Maniatis T. et al., Molecular Cloning: A Laboratory Manual, Cold Spring Harbor Laboratory, Cold Spring Harbor, New York). Libraries were created as follows. RNA from *Z. mays* tassels was isolated using a guanidine thiocyanate method followed by banding in a cesium chloride gradient. Poly A+RNA was selected using oligo dT cellulose. Two cDNA libraries were constructed in the vectors pCDNAII (Invitrogen) and Uni-Zap XR (Stratagene) using 5 ug of MRNA for each according to the manufacturer's instructions.

Figure 4:
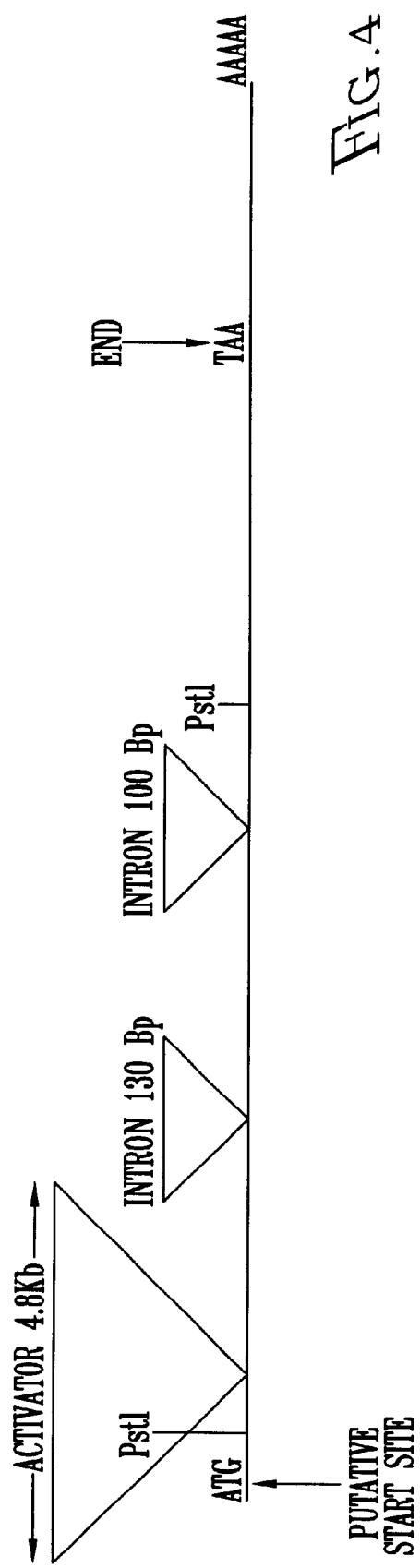
FIG. 4 is a graphic representation of the 1.4 kb DNA isolate and its intervening sequences.

The 1.3 kb inverse PCR product was probed onto the arrayed cDNA tassel library of about 1000 clones and from this a single homologous clone with an insert size of about 1.4 kb obtained. It was 1550 base pairs and is graphically depicted in FIG. 4. The genomic piece will, of course, vary according to the background of the plant from which it is isolated and the introns may or may not be present. This, however, shows how the Ac element appeared in this isolate.

Figure 5:
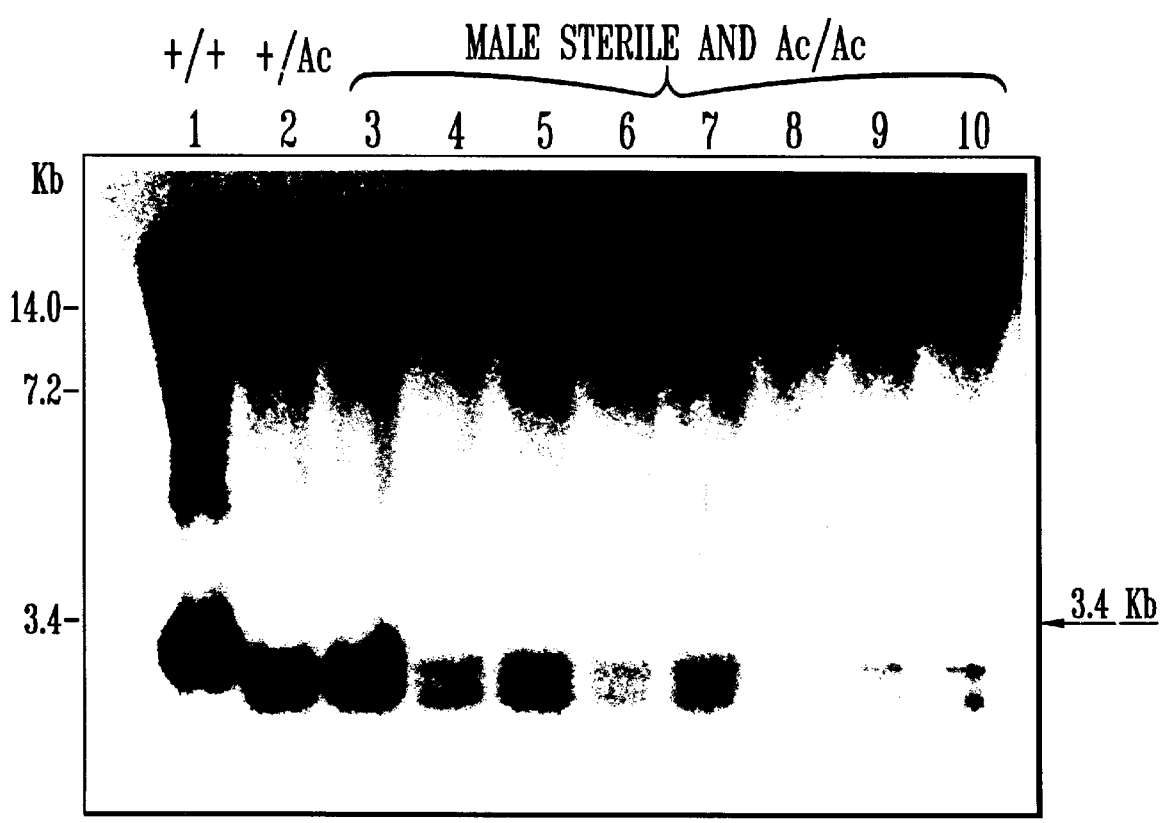
FIG. 5 is a Southern Blot analysis gel of Pvull digested DNA of an Ac family segregating for sterility and hybridized with the 1.4 kb DNA isolate.

The 1.4 kb was hybridized to the PvuII segregation membrane to insure the 3.4 kb co-segregating band found with the inverse PCR product was a new genomic region and not small amounts of Ac DNA contained on the ends of the fragment. The results are shown in the gel in FIG. 5. As can be seen, the 1.4 kb from the library hybridized in sterile plants to the same 3.4 kb fragment that co-segregated with the male sterile phenotype and the purple spotted kernels plants from the fertile heterozygous.

The 1.4 kb segment was then used against a second cDNA tassel library and the full length cDNA was obtained, and named MS45.

Northern Analysis

Figure 6:
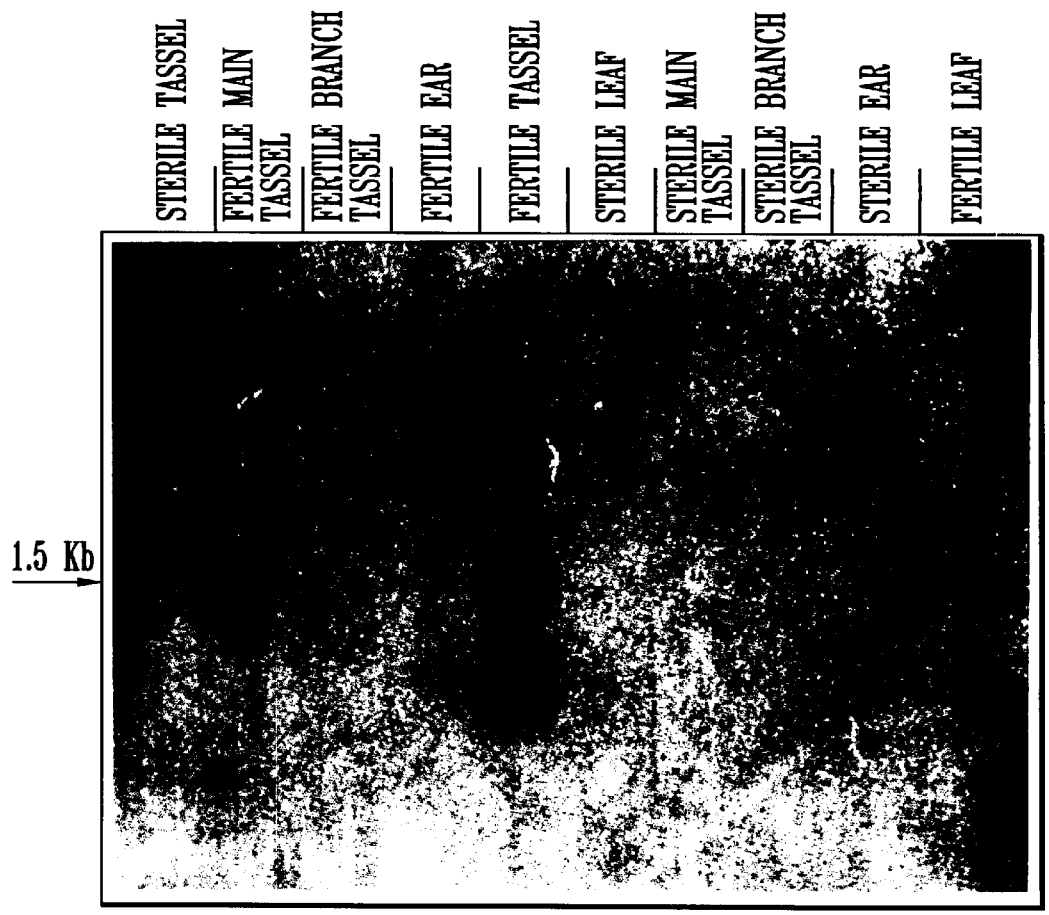
FIG. 6 is a Northern Blot analysis gel hybridized with the male fertility gene MS45.

Tissue from tassels, ears and leaves of sterile and fertile plants was isolated as described previously, and a Northern Blot analysis run on the extracts. Northern analysis is also a commonly used technique by those skilled in the art and is similar to Southern analysis except that RNA is isolated and place on an agarose gel. The RNA is then hybridized with a labelled probe. Potter, E., et al., "Thyrotropin releasing hormone exerts rapid nuclear effects to increase production of the primary prolactin MRNA transcript," Proc. Nat. Acad. Sci. USA 78:6662–6666 (1981); Lechelt, et al., supra. Total RNA was isolated from 1) leaves of plants grown approximately 2 months; 2) tassels at roughly the mid-vaculate stage; and 3) immature ears between 4.5–5.0 cm in length. Tissue was ground in liquid nitrogen then sequentially treated with a detergent extraction, a differential UCI precipitation, and an ethanol precipitation. The gel was hybridized with the MS45cDNA isolated as described above. The cDNA hybridized only with DNA from fertile tassels as can be seen in FIG. 6.

Revertants

To further confirm the gene as one critical to male fertility, revertants were identified. Since it would not be possible to distinguish normally fertile plants from revertants, plants were selected that showed sterility, but shed some pollen. These were crossed as males to unrelated lines and no male sterile plants resulted. The MS45 DNA was recovered and analyzed to find the Ac had left a "footprint" when transposing out of the gene of six base pairs, keeping the sequence in frame. See FIG. 7, showing two amino acids are added, but the frame does not shift.

I RFLP Mapping

Figure 8:
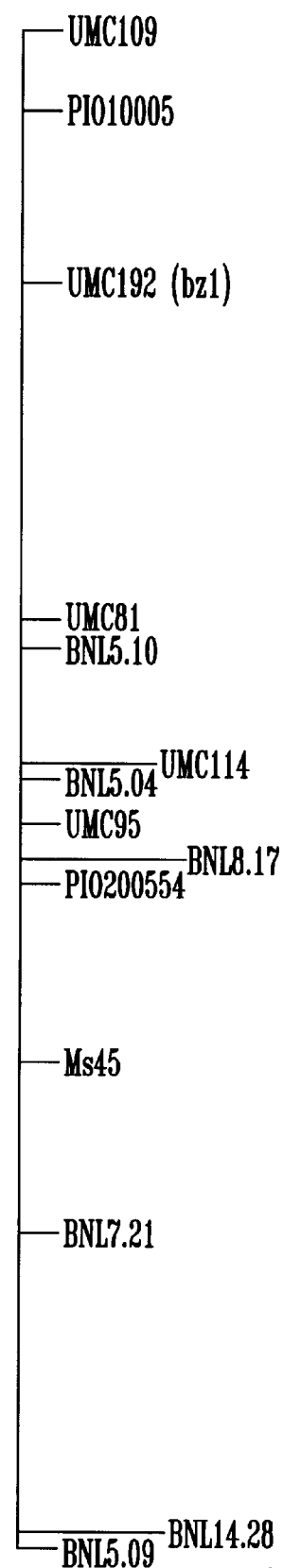
FIG. 8 is an RFLP map of chromosome 9 showing the male fertility gene MS45.

The IPCR fragment was RFLP-mapped in a B73 X Mo17 F2 population. It mapped to chromosome 9 L between probes and Burr 7.21 as described in Maize Genetics Cooperation Newsletter, 67:165 (Mar. 15, 1990) and depicted in FIG. 8.

Sequencing

Sequencing of the MS45 done was accomplished using the dideoxy chain termination method of Sanger, et al., Proc. Nat. Acad. Sci. USA 74:5463–5464 (1977).

By referring to MS45 DNA, it is to be understood that what is meant is a DNA sequence as set forth below which produces the amino acid sequence also set forth below. One skilled in the art readily appreciates that more than one three member codon may encode the same amino acid sequence.

EXAMPLE 2

Flavonoid Regulating Genes

Flavonoids are an abundant class of small molecular weight (-300) plant-specific metabolites which share a common 15 carbon skeletal structure. Modification of the basic structure yields an extensive array of compounds that are classified by the oxidation state and substitution pattern of the various rings. Some classes are pigments (e.g., anthocyanins, chalcones, and particular flavonols and flavones) while other classes are colorless ultraviolet-absorbing compounds. The anthocyanins, particularly pelargonin, cyanidin, and delphinidin, are responsible for the red, blue, and violet plant colors. Other pigmented flavonoids, the chalcones, and some flavonols and flavones are yellow and contribute significantly to the yellow, ivory and cream colored flowers. Pollen flavonoids have been identified in several species where they impact a distinctive yellow color to pollen and can account for a large percentage (2%–5%) of the dry weight (R. Zerbak, M. Bokel, H. Geiger, D. Hess, 1989, Phytochemistry 28;897; R. Wierinann and K. Vieth, 1983 Protoplasma 118;230). There is evidence that the pollen grain is a special environment for flavonoid biosynthesis and/or accumulation as several plant species have unique types of flavonoids in their pollen (O. Ceska and E. D. Styles, 1984, Phytochemistry 23:1822). Plants having modified flavonoid pigmentation have been previously reported in the literature. For example, a maize mutant producing non-functional white rather than yellow pollen has been previously isolated and characterized (Coe E. H., McCormick S. M. and Modena S. A., 1981, "White Pollen in Maize," J Hered 72:318–320). The white pollen mutant sheds normal amounts of non-pigmented pollen which germinates on the silk, but no seed is set after most pollinations. The condition is sporophytically determined by the expression of stable recessive mutations at the two chalcone synthase (CHS) genes in maize, C2 and Whp. Recently, Agrobacterium-mediated introduction of a CHS transgene into a pigmented inbred petunia stock was reported to suppress the expression of the endogenous CHS gene(s), resulting in flower corollas completely lacking flavonoid pigmentation (Napoli C., Lemieux C. and Jorgensen R., 1990, "Introduction of a Chimeric Chalcone Synthase Gene Into Petunia Results in Reversible Co-repression of Homologous Genes in Trans," Plant Cell 2:279–289). CHS transgene is also suppressed in these plants, and the term co-suppression has been used to describe this phenomenon (Jorgensen R., 1990, "Altered Gene Expression in Plants Due to Trans Interactions Between Homologous Genes," Trends Biotech 8:340344). The integrated transgene acts like an unlinked dominant inhibitor of the endogenous CHS gene(s) and leads to a complete block in the production of visible flavonoid pigments not only in flower petals but also reproductive organs.

Blockage of CHS gene expression not only results in flavonoid pigmentation deficiencies, but also in plants that are not fertile (Coe, et al., 1981; Taylor, et al., 1992, "Conditional Male Fertility in Chalcone Synthase Deficient Petunia", J. Hered., 83:11–17). Flavonol, and in particular, certain flavonols, are critical to pollen function, and their production or lack thereof can control fertility and sterility.

Plant fertility in a flavonoid-deficient, conditionally male fertile (CMF) plant is restored by contacting pollen of the plant with fertility restoring flavonols effective to enhance germination of the pollen of the plant. In an illustrative example, suitable conditions may be obtained by contacting pollen of the plant with an amount of a fertility restoring flavonol effective to enhance germination and tube growth of the pollen of the plant. As used herein, the term flavonoid-deficient, conditionally male fertile or CMF plant is intended to include plants in which the chalcone synthase (CHS) or flavonone-3-hydroxylase (F3H) activity has been impaired, either naturally or transgenetically, to disrupt the natural production of flavonoids in the plant. Accordingly, flavonoid-deficient, conditionally male fertile plants will typically be pigment deficient, resulting in a white or pale coloration, and will typically be self sterile. Although the invention will be hereinafter described in detail in connection with CMF petunias and maize, other CMF plants may be similarly used in the practice of the invention.

In the natural flavonol biosynthetic pathway, chalcone synthase (CHS) condenses three molecules of malonyl-CoA and one molecule of p-coumaroyl to form chalcononaringenin, which is converted to naringenin spontaneously (at a low rate) and by the action of chalcone-flavanone isomerase (CHI). In the next step of the pathway, F3H catalyzes the addition of a hydroxyl group to the 3-position carbon of the C ring to produce a flavonol, which is required for fertility restoring activity in accordance with the present invention. The general pathway may be represented as follows:

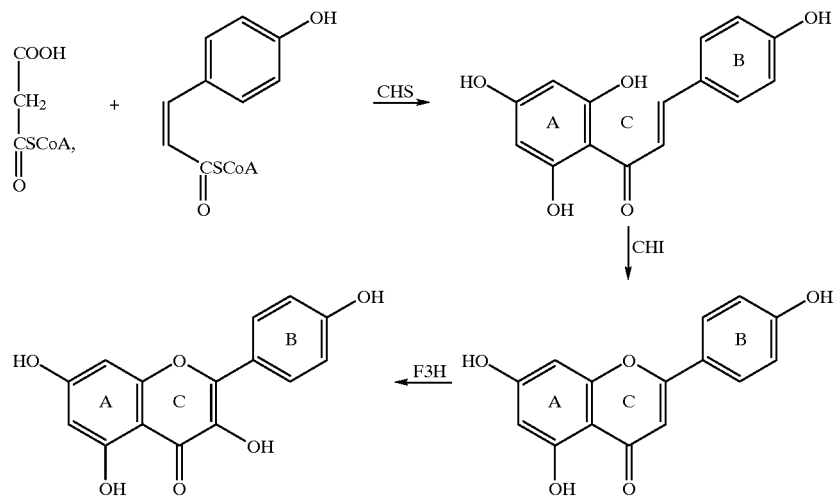

F3H is the rate limiting enzyme in the production of flavonols, and has been previously cloned from Antirrhinum majus (Martin, C., Prescott, A., Mackay, S., Bartlett, J. and Vrijlandt, E., 1991, "Control of Biosynthesis in Flowers of Antirrhinum majus," *The Plant J.*, 1:37–39). Since flavonol aglycone compounds are required for male fertility, as described here, an inducible promoter controlling the F3H hydroxiation activity may be employed in the practice of the invention.

Impairment of male function in plants which lack flavonoids as a result of a deficiency in CHS, CHI or F3H activities result in no gross abnormalities in pollen development until immediately prior to dehiscence when the anther morphology deviates from normal in color, shape, and size. At dehiscence the pollen remains clumped within the anther and when viewed microscopically a significant proportion of the grains in a locule appear more shrunken than normal. Although viable pollen is produced and shed, pollen germination and tube growth are greatly impaired both in vivo and in vitro. In addition to functional male sterility, flavonol-deficient plants exhibit some aspects of self-incompatibility, as evidenced by the fact that the pollen can be partially rescued by stigmas of wild type plants, but not by stigmas of flavonol-deficient plants. Although elements of both male sterility and self incompatibility are evident, the features exhibited by pollen from the flavonol-deficient plants clearly constitute a unique state which is referred to herein as conditional male fertility (CMF).

Plants lacking CHS (and therefore lacking flavonoids) appear normal except for two features: (1) a lack of flavonoid pigmentation and (2) the production of impaired pollen that is entirely dependent on wild pistils (stigma+ style) in order to function.

While CHS deficient plants share a lack of flavonoid pigmentation and pollen function impairment, some differences are evident between plant species. Maize white pollen germinates on the silks and produces a pollen tube whose growth is arrested in the style. Additionally, the maize mutant pollen germinates in vitro and produces a tube nearly as long as wild-type pollen. In contrast, pollen from the CHS-deficient petunia does not penetrate the stigma nor produce a tube either in vivo or in vitro. This difference between maize and petunia may be explicable in terms of the physiological differences between tricellular (maize) and bicellular (petunia) pollen. Bicellular pollen has a low respiratory rate when shed, forms the second sperm cell after shedding, may be on the sigma several hours before germination and has a low initial pollen tube growth rate. Tricellular pollen, by comparison, undergoes the second mitotic division before anthesis, has a high respiratory rate when shed, germinates within minutes after contact with the stigmatic surface and has a high initial growth rate. Because tricellular pollen is poised to grow rapidly after shedding, maize white pollen tubes grow to a significant length before any mechanism that arrests tube growth is effective.

In flowering plants with alternating generations, the diploid sporophyte produces haploid spores which grow and divide mitotically to produce the gametophyte. Part of the gametophytic life cycle occurs while the developing pollen spore is in intimate contact with surrounding sporophytic tissue. This arrangement has the potential for diploid-haploid interactions. In heterozygous plants this interaction would also include haploid-haploid communication between the two types of gametophytes as represented in FIG. 9. The fact that the petunia flavonoid-deficient male sterility described here is genetically dominant while the maize white pollen male sterility is genetically recessive leads to an interesting conclusion regarding whether the gametophyte or the sporophyte is responsible for the effect. In maize, male sterility is expressed only in plants homozygous recessive for both CHS genes, c2 and Whp. Heterozygotes with either a single functional copy of C2 or Whp produce 100% yellow, fertile pollen grains (Coe, et al. 1981). Thus, in the heterozygote either the CHS-positive sporophyte or the 50% CHS-positive gametophytes influence the expression of fertility in the CHS-negative gametophytes. In the transgenic petunia, male sterility is associated with a dominant trait and pollen produced by the heterozygous plants is 100% male sterile. In this case, sterility is caused either by inhibition of the CHS-positive gametophytes by the CHS suppressed gametophytes or by CHS deficiency in the transgenic sporophyte (FIG. 9). The physiological basis for CHS deficiencies causing male sterility appears to be the same in maize and petunia, and in both species it is the sporophyte that causes the sterile phenotype, rather than the gametophyte. Thus, the conditional male fertility associated with CHS deficiency in maize and petunia has a common physiological basis.

Control of fertility by regulation of flavonol production is evident by the fact it has been found it is possible to exploit the production of conditionally sterile pollen from the CHS-deficient plants to form the basis of an in vitro pollen rescue assay. By incubating the transgenic pollen in germination solution supplemented with purified flavonoids or plant extracts and assaying for enhanced germination frequency and pollen tube growth, specific compounds required for pollen function can be identified. In this manner, it has been determined that the broad family of flavonoid compounds, in general, is not uniformly effective in restoring fertility in CMF plants, but rather that a specific group of fertility restoring flavonol aglycones is effective for this purpose.

Any flavonol which is effective in promoting germination of pollen of a CMF plant may be used in the practice of the invention. It has been found, however, that most members of the relatively large family of flavonoids are ineffective for this purpose. Particular effective fertility restoring flavonols can be identified and used in the restoration of plant fertility in a CMF self sterile condition. In a preferred embodiment of the invention, the fertility restoring flavonol is a compound of the formula:

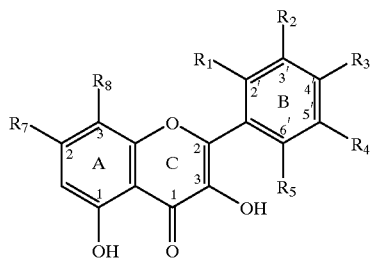

wherein R1, R2, R3, R4, R5, R7, and R8, are hydrogen, hydroxyl or alkoxy having from 1 to 3 carbon atoms. More preferably, not more than two of R1–R5 are hydroxyl or methoxy and the remaining R1–R5 are hydrogen, and R7 and R8 are hydrogen, hydroxyl or methoxy. Presently particularly preferred and representative fertility restoring flavonol compounds of the invention include galangin, kaempferol, iso-rhamnetin, quercetin, and morin which have the general chemical structure set forth above with the following substituents:

TABLE 2

| Flavonol | R1 | R2 | R3 | R4 | R5 | R6 | R7 |
|---|---|---|---|---|---|---|---|
| galangin | H | H | H | H | H | OH | H |
| kaempferol | H | H | OH | H | H | OH | H |
| Iso-rhamnetin | H | OCH3 | OH | H | H | OH | H |
| quercetin | H | OH | OH | H | H | OH | H |
| morin | OH | H | OH | H | H | OH | H |

Other flavonols useful in the practice of the invention may be readily determined using the in vitro pollen rescue assay methods set forth herein.

The foregoing may be better understood in connection with the following embodiments, which are presented for purposes of illustration and not by way of limitation.

Fertility of Chalcone Synthase-deficient Petunias

Transgenic and inbred V26 petunia were maintained on a 1618 hour photo period in a glass house supplemented with metal halide lights at an intensity of 300–600 pmol m-2 sec-1. Inbred V26 is a pigmented line of Petunia hybrids which can produce flavonoids in most plant tissues including pollen, anthers and filaments, and pistil (stigma+style) and is fully self-compatible. The transgenic material analyzed consisted of the two independent transformed regenerants, 218.38 and 218.41 (Napoli C., Lemieux C. and Jorgensen R., 1990, "Introduction of a Chimeric Chalcone Synthase Gene Into Petunia Results in Reversible Co-Repression of Homologous Genes In Trans," *Plant Cell* 2:279289) and individuals from the second backcross generations (BC2) to the parental V26 line (population numbers 2425 through 2435). The T-DNA insertion in these transformants contains CHS cDNA sequences fused to a viral promoter linked to a neomycin phosphotransferase II gene as a selectable marker (Napoli, et al. 1990). Crosses were performed by emasculating flowers 24 hours prior to the application of pollen. All transgenic flowers used for crosses showed no visible signs of pigment. Pollen donors were selected from plants that had 2 to 3 dehiscent anthers or dissected from plump, pre-dehiscent anthers as noted.

The transgenic petunia plants 218.38 and 218.41 where pure white flowers after the introduction of an additional copy of the CHS gene. When CHS expression was examined in the transgenic petals, a 50-fold induction in mRNA compared to the untransformed V26 parent or somatic revertants was detected in both endogenous and introduced CHS genes. The V26 inbred line produces purple anthocyanin pigments in leaves, stems, pedicles, styles and anther filaments, and yellow chalcones in developing anthers. In comparison, the transformed plants have no discernible flavonoid pigments in any of these tissues. The lack of visible pigment has been confirmed by HPLC analysis of methanolic extracts as described below under "UV effects". Normally, just prior to shedding, petunia anthers filled with mature pollen undergo desiccation. At dehiscence, when the anther case ruptures longitudinally along the stomium, the dehydrated state of the tissue results in the two edges of the anther lobe curling back on one another to expose the pollen grains. Close inspection of the non-pigmented transgenic plants reveals that, in the 48 hours preceding dehiscence, the anthers shrink an average of 40% in length and change in color from creamy-white to tan. In comparison, the anthers of the non-transformed parental line V26 shrink only about 15% and do not undergo a color change, remaining yellow throughout this period. A wide variation in the frequency of dehiscent anthers occurs ranging from 0 to 100% with the higher frequency associated with lowered relative humidity. Although dehiscence may be slightly delayed relative to the V26 parent, the CHS-deficient anthers do open to expose normal amounts of pollen which does not appear as light and friable as V26 pollen and remains dumped within the anther case.

No seeds resulted from numerous attempts at self pollination of the flavonoid-deficient progeny of 218.41 using either (i) pollen from shrunken, tan, dehiscent anthers or (ii) pollen dissected from white, plump, pre-dehiscent anthers (see Table 3, column 5, "Transgenic Self Crosses: 0 seeds/ pod"). Self crosses of the V26 parent line produce on average 225 seeds per pod. This translates to approximately 17,000 possible seeds in the 75 transgenic petunia self crosses that were attempted. All of the plants listed in Table 2 were tested for female fertility by pollinating stigmas with pollen from inbred line V26. In all cases, pods were produced with the normal complement of seeds, indicating that the CHS-deficient plants are female fertile. The reciprocal cross, transgenic flavonoid-deficient pollen onto V26 stigmas resulted in the production of varying quantities of seeds as shown in Table 3.

TABLE 3

Seed Production From Transgenic Pollen Crosses
NUMBER OF POLLINATIONS

| Pollen | V26 X transgenic pollen | | | Transgenic self crosses |
|---|---|---|---|---|
| Parents | 0 seeds/pod | 1–150 seeds/pod | >150 seeds/pod | 0 seeds/pod |
| 02425.1* | 0 | 2 | 0 | 8 |
| 02430.5 | 0 | 5 | 3 | 6 |
| 02430.6 | 2 | 1 | 0 | 6 |
| 02430.8 | ND | ND | ND | 6 |
| 02432.2 | ND | ND | ND | 6 |
| 02435.1 | 0 | 1 | 1 | 6 |
| 02435.2 | 1 | 4 | 1 | 8 |
| 02435.3 | 0 | 1 | 1 | 7 |
| J2425.1* | 0 | 1 | 0 | 1 |
| J2428.1 | ND | ND | ND | 6 |
| J2431.2 | 2 | 3 | 0 | 6 |
| J2432.3* | 3 | 0 | 0 | 7 |
| J2430.5* | 3 | 2 | 0 | 2 |

*Flowers on other branches of this plant had some purple pigment in corolla.
*At least 4 flowers on each plant listed was pollinated with V26 pollen and all set full seed pods.
Average number will/pod = 225.

Of 37 crosses involving 10 different transgenic plants as male parents, 11 produced no pods, 20 produced pods with less than 150 seeds per pod and 6 produced pods with greater than 150 seeds per pod. This averages to approximately 60 seeds per pod or a 70% reduction in seed set. These results indicate that while pollen from the flavonoid-deficient plants is non-functional on flavonoid-deficient stigmas it is partially functional on wild type stigmas, the state we termed herein as conditional male fertility (CMF). The wide variation in the number of seeds set per pollination in these outcrosses is possibly due to environmental and/or developmental factors.

It is unlikely that CMF is due to the insertion of T-DNA into a gene required for male fertility since two independent transformants, 218.38 and 218.41, both display the same features: a complete lack of flavonoid pigmentation and identical dominant male sterile phenotypes. Additional evidence for this conclusion comes from the observations of Napoli et al. (1990) that the transformed regenerants sometimes revert somatically to fiery pigmented plants but retained the transgene, indicating that the presence of the transgene alone does not suppress endogenous CHS expression.

Given the similarity with white pollen in maize, CMF in petunia appears to be caused by a deficiency in flavonoids, such as that caused by a suppression of CHS or F3H gene expression.

Pollen Germination and Tube Growth

In vitro germination was performed on freshly collected pollen in simplified Brewbakers medium as described in Mulcahy GB and Mulcahy DL, 1988, "The Effect of Supplemented Media on The Growth in vitro of Bi- and Trinucleate Pollen," Plant Science 55:213–216 (herein sometimes referred to as "germinating medium" or "GM"). Pollen from a single anther was placed in a microtiter well with 50 μl of media, rocked at room temperature for 6 to 8 hours and photographed with Kodak technical pan film.

In vivo pollen tube growth was measured 48 hours post-pollination as described in Herrero M. and Dickinson H. G., 1979, "Pollen-pistil Incompatibility in Petunia Hybrids: Changes in the Pistile Following Compatible and Incompatible Intraspecific Crosses," J. Cell Sci, 36:1–18. Callose plugs were visualized by epifluorescence generated by excitation at 355–425 mn (D cube) and suppressing wavelength 460 nm from a Leitz Aristoplan. Specimens were photographed with Ektrachrome T 160 film and prints made from an internegative.

Pollen viability was determined with the fluorochromatic procedure (FCR) (Heslop-Harrison J. and Heslop-Harrison Y. 1970, "Evaluation of Pollen Viability by Enzymatically Induced Fluorescence; Intracellular Hydrolysis of Fluorescein Diacetate," Stain Technol 45:115–120) by incubating freshly dehiscent pollen in a solution of carboxyfluoresceine acetate (1 mM) in germination media. Epifluorescence was visualized as described above.

Callose Production

Petunia pollen tubes normally penetrate the stigma about one hour after germination (Herrero and Dickinson 1980) and grow downward through the styler tissue to deposit the two sperm cells in the embryo sac. Callose is a polysaccharide polymer-linked in $\beta(1-3)$ glycosidic linkages and plugs of this material are normally deposited at regular intervals down the growing pollen tube. Callose is visualized by its distinctive fluorescence after staining with decolorized aniline blue (Currier 1957; Eschrich and Currier 1964). The germination and growth of pollen tubes in self crosses of CHS-deficient flowers and in backorosses of the same plants with V26 pollen were examined. Pistils were harvested 48 hours after pollination, stained with decolorized aniline blue and examined by fluorescent microscopy. A regular pattern of callose deposits was observed all the way down the style in the squashes of flavonoid-deficient pistils pollinated by V26. On the other hand, no callose was seen in the pistils of the self pollinated petunias even though copious amounts of pollen was present on the stigma.

Pollen Morphology and Germination

Figure 10A:
FIGS. 10A and 10B are photographic representations of in vitro germinating pollen from inbred petunia line V26 (FIG. 10A) and CHS-deficient plant O2425.1, wherein the pollen from freshly dehiscent anthers was suspended in a liquid medium and photographed after growth at room temperature for 6 hours. The bar in FIG. 10A represents 25 $\mu$m. The arrows in FIG. 10B indicate pollen tubes attempting to germinate.
Figure 10B:
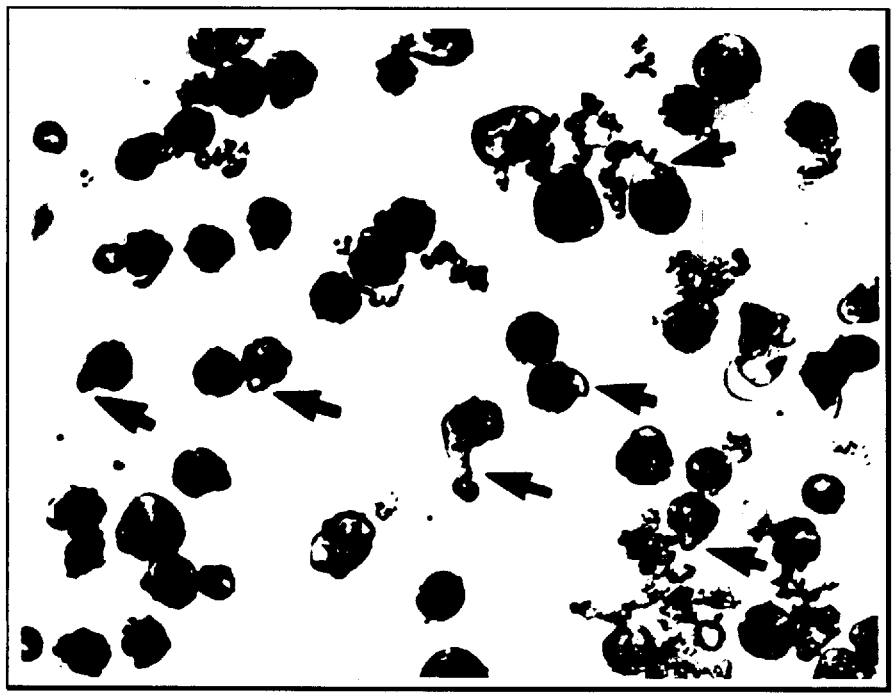

A microscopic examination of freshly shed pollen from flavonoid-deficient plants described supra (Fertility of Chalcone Synthase-Deficient Petunias) was made and did not reveal any gross abnormalities. Petunia pollen readily germinates and produces a tube when incubated in a simple liquid medium. Germinated pollen from each of the BC2 families (2425 to 2435) to V26 pollen were compared in vitro. A typical representative is shown in FIG. 10. As shown, after 6 hours of growth many mutant pollen grains have attempted germination as noted by the pronounced swelling around one of the germination pores (arrows, FIG. 10), but at most only 2% of the pollen grains from the CHS-deficient plants produce a tube of any length. Of the pollen grains that do produce measurable tubes, the length is less than 20% of the length of V26 pollen tubes grown under identical conditions.

To determine whether the pollen produced and shed by the flavonoid-deficient plants was viable and therefore capable of germination and pollen tube growth, a fluorochromatic analysis (FCR) for viability on freshly shed transgenic and V26 pollen was performed. This test depends on the uptake of a fluorescein diacetate compound into the pollen grain with subsequent conversion to fluorescein by intracellular enzymes. Fluorescein is highly polar and remains sequestered, most likely in the vegetative cell cytoplasm, where it is visualized by fluorescent microscopy. Inbred V26 pollen consists of a high proportion (up to 40%) of abnormally small, FCR negative grains which entirely lack any internal features. Several grains of this type can be seen in FIG. 10A, including two in the center of the photograph. This population never germinates and is most likely aborted grains. Of the remaining grains (60%), almost all showed a positive FCR test, indicating the presence of intact plasma membranes and active cytoplasmic esterases. Pollen from the mutant anthers retains the high proportion of shrunken, aborted grains. Of the remaining normal appearing grains, more than 90% were FCR positive. The fact that most of the pollen produced by the flavonoid-deficient plants was viable and metabolically active indicates that some aspect of flavonoid activity is required for normal pollen germination and tube growth.

Microscopic Observations of Anther Development

Figure 11A:
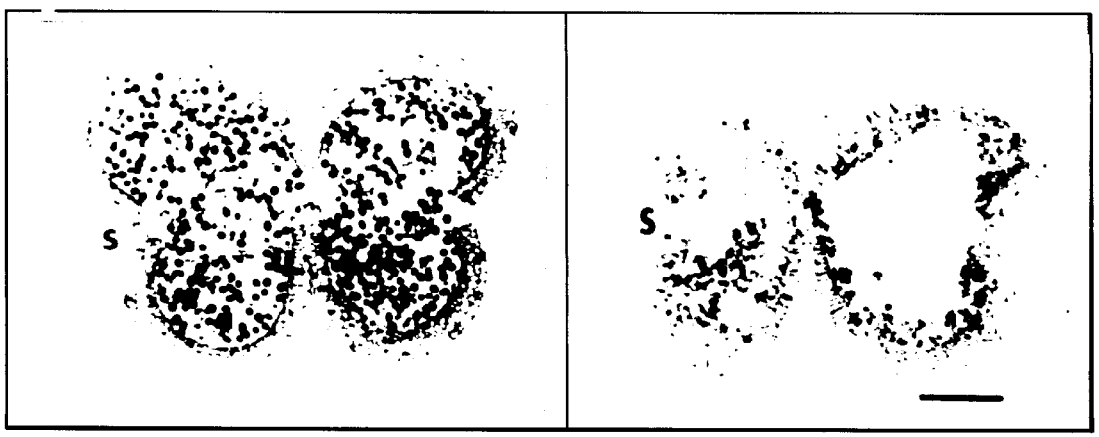
FIG. 11A shows whole anther sections immediately before dehiscence when CHS-deficient anthers are tan and shrunken. The bar in FIG. 11A represents 200 $\mu$m.
Figure 11B:
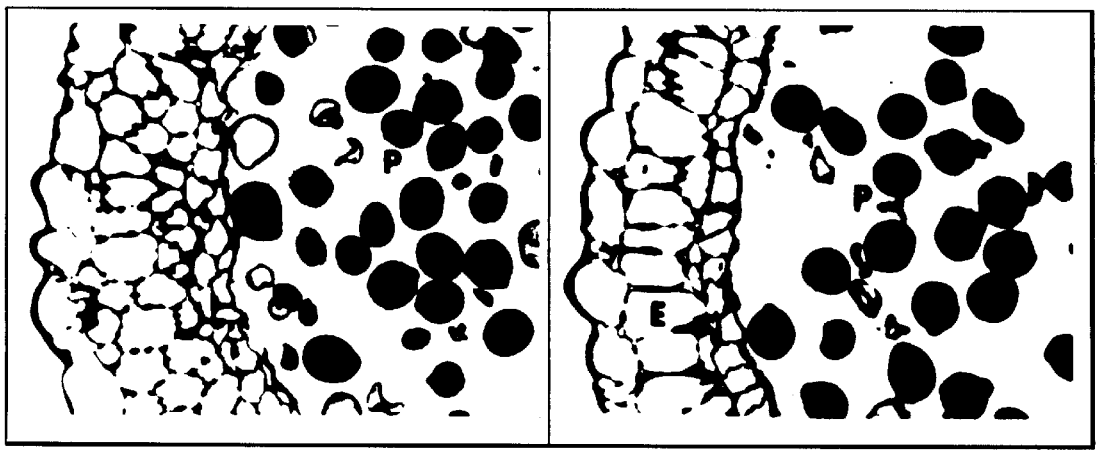
FIG. 11B shows anther sections 48 hours before dehiscence when transgenic anthers are plump and white.
Figure 11C:
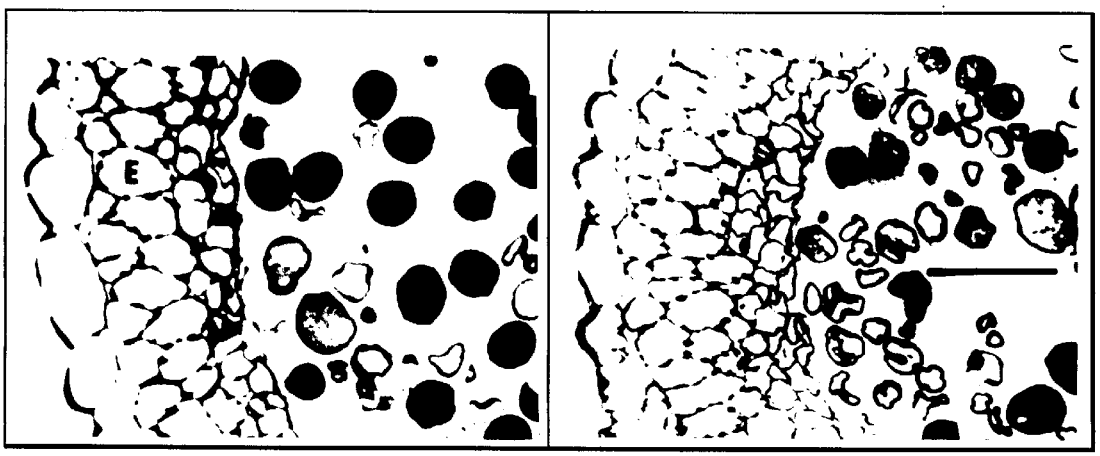
FIG. 11C shows anther sections as FIG. 11A at the magnification of the representations of FIG. 11B. The bar in FIG. 11B represents 50 $\mu$m.

To determine if the lack of flavonoid activity during microsporogenesis altered the cellular architecture of the developing pollen grains or anther tissues, pollen development in V26 and flavonoid-deficient plant 02425.1 was compared. Anthers from a developmentally staged series of petunia buds ranging in length from 0.1 to 6 cm. were harvested, fixed in 2% paraformaldehyde, 1.25% gluteraldehyde in Pipes, pH 7.Z embedded in Spurrs resin and 1 $\mu$m sections were stained with toluidine blue. Photomicrographs were made with Kodak technical pan film. Histologically this represents all stages of microsporogenesis, from the earliest evidence of archesporial tissue differentiation to pre-dehiscent anthers filled with mature pollen. Close attention was given to the development, and subsequent disintegration of the tapetum, since this tissue is thought to be the source of pollen flavonoids. At all stages, the transgenic anther and developing microspores showed no gross histological differences when compared to V26. Additional sections were taken from the flavonoid-deficient anthers during the transition from plump, white to shrunken, tan and compared to similar stages in V26 (FIG. 11). Preceding dehiscence the cells of the endothelial layer normally expand radially, thicken, and deposit material which is thought to be involved in the mechanism of anther rupture (Cutter, E.G., 1978, "Plant Anatomy: Experimentation and Interpretation, Part I", *Cells and Tissues,* 2nd Ed., Landon: Arnold). This layer is not continuous, being absent in the area surrounding the stomium. The sections of the shrunken, tan anthers show no gross abnormalities to the endothelial layer, stomium, or cuticle surrounding the anther. However, when compared to V26 pollen (FIG. 11, Column "V26") a higher proportion of shrunken grains devoid of internal features were present in the locules of the transgenic plants and the larger grains appeared more heterogeneous in size, shape, and staining reaction (FIGS. 11C and 11D). The heterogeneity shown in FIGS. 11C and 11D may be accounted for by the fact that pollen is normally shed in a highly dehydrated state and undergoes rapid rehydration on the stigma. Flavonoid-deficient pollen may be shed in a much more dehydrated state than normal, and when placed in liquid germination medium, appears to rehydrate to a normal appearance.

Petunia Flavonoid Extracts

Analyses of petunia pollen extracts have identified the major flavonoids as 3-0-glycosides of quercetin and kaempferol, 4, 2', 4', 6'-tetrahydroxychalcone, and a dihydroflavonol, taxifolin (Zerback, R., Bokel, M., Gieger, H. and Hess, D., 1989, *Phytochemistry* 28:897–899; Zerback, R., Dressler, K. and Hess, D., 1989, *Plant Science* 62:83–91; De Vlaming, P. and Koh, K. F. F., 1976, *Phytochemistry* 15:348–349). Maize pollen contains at least 10 glycosides of kaempferol, quercetin, and isorhamnetin (Ceska, O. and Styles, E. D., *Phytochemistry* 23:1822–1823). Aqueous extractions from both wild type and inbred petunia line V26 were made by macerating stigmas with forceps or vortexing a pollen suspension in PEG 4000 media (w. Jahnen, W. M. Lush, A. E. Clarke, 1989, *Plant Cell* 1:501), hereafter referred to as GM, centrifuging 5 min in a microfuge, and applying aliquots of the supernatant directly to a CMF pollen suspension in GM in a 96 well microtiter plate. Methanol extraction followed the same protocol except the extract was dried under vacuum and resuspended in GM before addition to the pollen suspension. The initial rescue experiment elicited a 33% gemnination rate using 20 $\mu$l (one-fifth total volume) of an aqueous extract prepared from ten V26 stigmas. As a control, extracts were prepared in a similar manner from stigmas and pollen of the CMF plants. In pollen germination assays only extracts from V26 stigmas and pollen were able to restore germination and tube growth to the flavonoid-deficient pollen.

The wild type and CMF pollen and stigma extracts were analyzed as follows. Stigmas or pollen were extracted first with 50% methanol, followed by 100% methanol, and the extracts were pooled and concentrated. Aglycones were produced by acid hydrolysis: the extract was mixed v/v with 4N HCl sealed in a 2 ml ampule and hydrolyzed in boiling water for 40 min. Replicate samples were injected into a reverse-phase C18 column (Phenomenex Spherisorb 5 ODS 2 250×4.6 mm). Solvent A was 5% acetic acid and solvent B consisted of 5% acetic acid in 80% acetonitrile. Each run consisted of a 6 min isocratic gradient (20%B), followed by a 20 min linear gradient to 90% B and terminated isocratically at 95% B for 14 min. The solvent flow rate was 0.5 ml/min at room temperature. Detection was at 360 nm with a Hewlett Packard Model 1040A photodiode array detector. Kaempferol was detected in the wild type stigma extracts at 60 ng sigma, and quercetin at substantially lower levels. Identical extracts from a pool of 150 CMF stigmas or from 500 CMF anthers yielded no peaks giving a typical flavonol spectra.

Treatment of the wild type stigmatic extract with protein digesting enzymes, heat, and passage through molecular sizing membranes indicated that the active compound was a small non-proteinaceous molecule. The molecular weight of the active compound was estimated by passing the extract through a 3000 dalton molecular weight cutoff filter (Centricon-30 filter, Amicon) and establishing that the pollen rescue activity passed through the filter. Aqueous extracts of V26 stigmas and pollen were treated with 0.025 units of papain for 30 min at 37° C. in a 100 $\mu$l reaction volume. Enzyme activity was verified by treating BSA (0.5 mg/ml) under the same conditions and by examining the digestion products by SDS-polyacrylaminde gel electrophoresis (PAGE). Neither the protease nor a heat treatment (100° C., 5 min) eliminated the ability of the extracts to rescue CMF pollen germination and tube growth.

Collectively, these results indicate that the flavonoids present in wild type pollen play a role in pollen germination and that the wild type stigma contains similar compounds which can compensate for the lack of flavonoids in the CMF pollen.

Flavonol Rescue of CMF Fertility

Biochemical complementation of the flavonoid-defident pollen described supra (Fertility of Chalcone Synthase- Deficient Petunias) was achieved by adding a low concentration (1 µM) of kaempferol, a flavonol aglycone, to a suspension of CMF pollen in germination medium (GM). As shown in FIG. 12, side-by-side comparisons made throughout a 12 hour growth period confirmed that germination initiated simultaneously and that tube growth proceeded at the same rate and to the same extent in the rescued CMF pollen (K+) compared to wild type V26 pollen which received no flavonol supplement (C). The rescue was nearly complete; the flavonoid-supplemented pollen showed an 80% germination frequency relative to V26 pollen. CMF pollen to which only the DMSO solvent was added (K−) showed no significant germination (1–2%) and the pollen tubes, if they germinated at all, never progressed more than 2 pollen grain diameters.

Figure 13A:
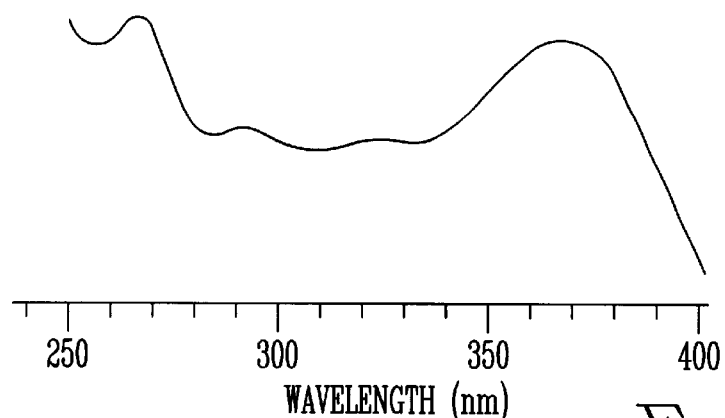
FIG. 13A is an HPLC profile of methanolic extracts of wild type V26 stigmas (FIG. 13B) and CMF stigmas (FIG. 13C). Absorption at 360 nm of 100 pi aliquots of extracts prepared from 150 stigmas and fractionated in a methanol-water gradient on a reverse-phase C18 column. The insert of FIG. 13B is the UV/visible spectrum of the peak at 33.17 min and is identical to that produced by an authentic kaempferol standard. An HPLC profile and UV/visible spectrum of an acid hydrolyzed V26 stigma extract indicates that the major peaks at retention time 7.43, 10.10, 13.46 and 16.65 are glycosides of kaempferol and quercetin.
Figure 13B:
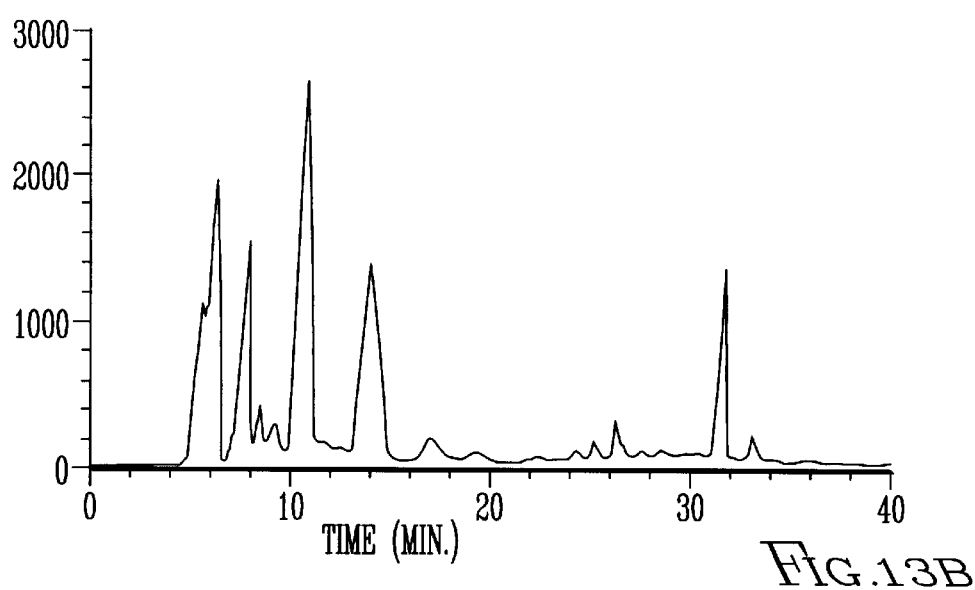
Figure 13C:
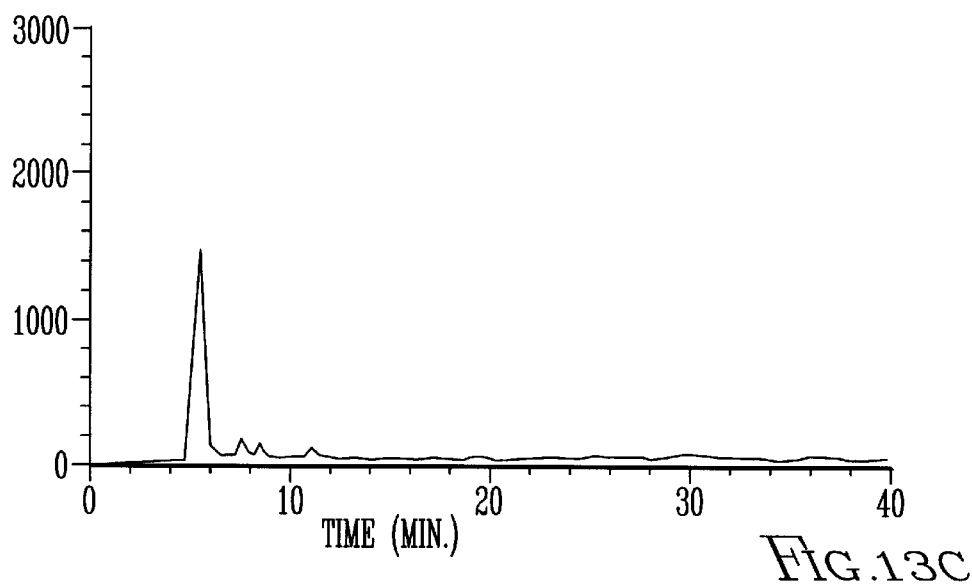
Figure 14:
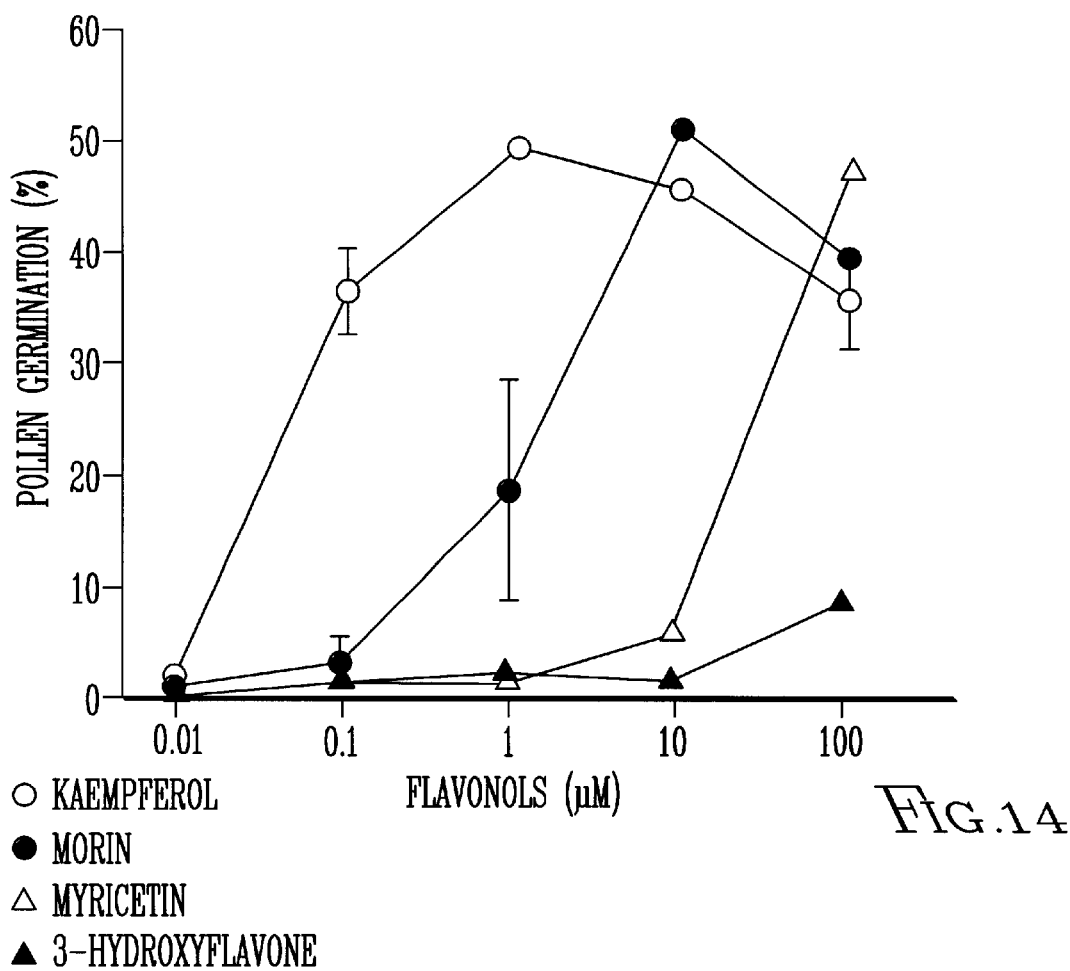
FIG. 14 is a graphical representation of pollen germination frequency as a function of increasing flavonol aglycone concentration, in which kaempferol (open circles), morin (closed circles), myricetin (open triangles) and 3-hydroxyflavone (closed triangles) were added to germinating medium (GM) at the indicated final concentrations and germination was scored after 4 hours of incubation. The mean germination frequency measured in three separate experiments is plotted with the standard error of the mean (SEM). SEM values <1.4 are not visible. The germination frequency of the wild type control V26 pollen is typically 75% and the non-rescued DMSO-treated CMF pollen yields between 1–2% pollination.

To confirm that wild style stigma extracts which are capable of rescuing pollen germination and tube growth contain kaempferol, unhydrolyzed extract was fractionated by HPLC and analyzed by UV/visible absorption spectroscopy. A peak with a retention time and typical flavonol spectra (absorption maxima around 260 and 360 nm) was detected in the V2 stigma extract (FIG. 13A and inset). This putative kaempferol peak was collected, evaporated to dryness, resuspended in DMSO and added to the in vitro GM media where it elicited a full germination and tube growth response from the CMF pollen. Re-chromatography of this active fraction with an authentic kaempferol standard confirmed its purity and identity. From this analysis of 150 stigmas, the amount of kaempferol in a V26 stigma is calculated to be 60 ng/stigma. By assuming a stigma volume of 34 µl (volume displacement), the flavonol concentration in a V26 stigma is about 6 µM, a level which is capable of eliciting a strong germination response. An identical analysis on extracts from a pool of 150 CMF stigmas or from 500 CMF anthers yielded no peaks giving a typical flavonoid spectra (see FIG. 13B). Extracts from V26 pollen and anthers produced a chromatogram similar to that shown in FIG. 13 and the eluent peak, with a retention time and UV/visible spectrum indicative of kaempferol, when added to CMF in GM fully stimulated pollen germination. This analysis confirms that kaempferol is present in wild type pollen and anthers.

Structural Features Required For Pollen Rescue Activity

Wild type pollen and stigma extracts from petunia contain other compounds in addition to kaempferol which may also stimulate pollen germination and tube growth (see FIG. 13A). Therefore representative compounds from all the major classes of flavonoids: flavones, flavonones, flavonols, isoflavonoids, chalcones, anthocyanins, and catechins were assayed for pollen rescue activity as follows. Petunia pollen grains were suspended in PEG 4000 germination medium (GM) at a density of 1–2×104/ml, and 100 pi aliquots of the suspension were placed in wells of a 96 well microtiter plate and were incubated at room temperature with shaking at 150 rpm. Any supplements were added directly to the GM before addition to the pollen. Stock solutions of flavonoids and other chemicals were made directly in dimethylsulfoxide (DMSO) and added to each well to the final concentrations indicated in the following Table 4. The concentration of DMSO was held constant in each essay at 1%. Pollen was scored as germinated when the tube was more than 1 pollen grain diameter long. Practically all grains that germinate go on to produce a tube longer than 5 pollen grain diameters. The CMF Petunia V26, as described supra (Fertility of Chalcone Synthase-Deficient Petunias) produces two types of mature pollen; about 25% of the grains are small with no internal features and they never germinate in vitro. Therefore, complete germination in V26 occurs when 75% of the total pollen grains have germinated. The CMF petunia pollen maintains this same ratio. In most rescue experiments the maximum germination frequency was 89% of the viable grains. After 4 hours incubation a minimum of 1000 pollen grains were scored in each assay. The lowest concentration of the tested compounds required to obtain a germination response are set forth in the following Table 4, wherein NR indicates no response. Compounds which cause <20% germination at 100 µM are indicated as >100 µM. In addition to the compounds listed in Table 4, the non-flavonoids p-coumaric acid, salicylic acid, hydroquinone, chlorogenic acid, dihydroascorbic acid, naphthylphthalmic acid (NPA), 1-napththalencacetic acid (NAA), indol-3-acetic acid (IM) and gibberellic acid (GA3) were tested and produce no response.

TABLE 4

| COMPOUND | CONCENTRATION FOR RESPONSE (µM) |
|---|---|
| Flavonols | |
| Galangin | 1 |
| Kaempferol | 1 |
| Iso-rhiamnetin | 1 |
| Quercetin | 10 |
| Morin | 10 |
| Myricetin | 100 |
| Fisetin | 100 |
| 3-hydroxyflavone | >100 |
| Dihydroflavonol | |
| Taxifolin | >100 |
| Flavone | |
| Flavone | NR |
| 7-Hydroxyflavone | NR |
| Apigenin | NR |
| Luteolin | NR |
| Flavonones | |
| Flavonone | NR |
| Naringenin | NR |
| Eriodictyol | NR |

As can be seen from Table 4, the aglycone flavonols successfully restored maximal germination frequency and tube growth capacity to the CMF pollen but among the other classes of flavonoids only the closely related dihydroflavonol, taxifolin, produced a modest (−18%) response at 100 µM (FIG. 12). Additionally, several classes of non-flavonoid compounds were tested including phenolic acids, anti-oxidants, and plant growth regulators but none were able to rescue pollen germination. Hence, the ability to rescue pollen function at physiologically relevant concentrations appears to reside in the flavonols.

From the range of flavonoids tested, five general structural requirements are identified for pollen germination and tube growth. There are absolute requirements for an unsubstituted hydroxyl group at the 3-carbon position and for a keto group at position 4 in the C ring. A maximal response depends on an unsaturated bond between carbons 2 and 3 in the C ring and the degree of hydroxyl group substitutions in the A and B rings. Most interestingly, flavonols glycosylated through the 3 hydroxyl position are inactive although they are by far the most abundant form of flavonols found in plant tissues, including petunia pollen and stigma. No pollen germination was obtained when quercetin-3-0-glucoside and rutin (quercetin-3-0-rhamnoglucoside) were tested at concentrations up to 100 μM. The requirement for a keto group at position 4 in ring C is indicated by the fact that catechin, which has no keto group lacks activity. A comparison of the relative efficiencies of taxifolin (~18% at 100 μM) and quercetin (~50% at 10 μM) shows that a double bond between carbons 2 and 3 in the C ring increases the response by about 30-fold. A comparison of quercetin with Fisetin or with 3-hydroxyflavone, shows that each additional hydroxyl group at either position 5 or 7 on the A ring increases the response approximately 10-fold. This increase may depend largely on the stabilizing effect of a interaction between the 5 hydroxyl group and the adjacent keto group in ring C. Finally, hydroxyl substitutions on the B ring are not necessary for full activity, and in fact increasing the number of groups actually causes a decrease in the activity (compare kaempferol with quercetin and muricetin). This difference could be due to poor uptake or an increase in non-specific binding caused by the mare polar nature of flavonols with numerous hydroxyl groups.

Some non-active flavonoids have been reported to antagonize active flavonoid-induction of nodulation genes in the Rhizobium-legume system (Djordjevic, M. A., Redmond, J. W., Batley, M. and Rolfe, B. G., 1987, EMBO 6:1173–1179; Peters, N. K., and Long, S. K., 1988, *Plant Physiology* 88:396400). The compounds that were nonactive in rescuing pollen function were tested for their ability to antagonize the action of the flavonol aglycones, as follows. CMF pollen, as described supra, in GM was exposed to inactive compounds at concentrations of 1 and 10 μM for 30 minutes before adding kaempferol to 1 μM. The experiment was also performed by simultaneously adding both the inactive compound and kaempferol at 1:1 or 10:1 ratios, to the pollen suspension. The pollen germination frequency was scored after 4 hours incubation and no antagonizing action was detected in any of the combinations tested. The following inactive compounds were analyzed: apigenin, chalcone, eriodictyol, flavone, flavanone, luteolin, naringenin, catechin, chlorogenic add, p-coumaric acid, hydroquinone, and salicylic acid.

UV Effects

In part because of their UV light absorbing capabilities, flavonoids are postulated to function as UV protectants in plants (W. Jahnen and K. Hahlbroch, 1988, *Planta* 173:453 and references therein). To determine if the lack of germination in the flavonoid-deficient pollent was due to UV effects, dark germination experiments were performed with three variations.

Pollen was harvested either from (1) flowers that were collected and stored (in water) in complete darkness for 24 hours or (2) freshly picked flowers. From these two sources pollen suspensions in GM with or without flavonols were prepared in a darkroom using a red safe light. The third variation involved preparing the pollen suspension from the freshly harvested flowers in the light but adding the flavonols solution in the dark. All specimens were wrapped in foil and incubated as described supra. There was no detectable effect of light on germination frequency for either the V26 control or the flavonoid deficient pollen, with or without added flavonols.

To determine if UV light affected self fertilizations, mature plants were grown for several weeks under a 610 nm filter petunia plants as described in L. P. Taylor and W. R. Briggs, 1990, *Plant Cell* 2:115. Petunia buds take about 2 weeks to form and mature, therefore only those buds that formed after the plants were placed under the filter were tested and thus were exposed to no light below 610 nm were self fertilized. No seed set occurred in any of the crosses 910 trials, but all V26 control self crosses performed under the same conditions set full seed pods.

Effect of Flavonol Exposure Time

The amount of flavonoid exposure required for complete germination and maximal tube growth was determined by varying the time the germination pollen was in the presence of flavonol. A concentration of kaempferol calculated to give near maximal rescue, yet easily removed by washing (0.5 mM final), was added to a 60×15 mm petri dish containing a suspension of flavonoid-deficient pollen in GM and the resulting suspension was continuously rotated at 150 rpm. At the times indicated in Table 5, 400 μl aliquots were taken, centrifuged, washed in 1 ml GM to remove the kaempferol, recentrifuged, resuspended in 400 μl GM, and split into two portions. One 100 μl aliquot was again supplemented to 0.5 mM kaempferol (control) but the other portion was allowed to continue growth without additional flavonol exposure (treated). Growth was allowed to proceed for a total elapsed time of 4 hours from the formulation of the original suspension, then germination frequency and tube length were scored in both treated and control germinations. The results are shown in the following Table 5:

TABLE 5

| | Treated Pollen | | |
| --- | --- | --- | --- |
| Exposure time- (min) | Germination (%)* | Tube Length** | Control Germination (%)* |
| 0 | 3.7 + 1.5 | 2x | 48.3 +/− 2.5 |
| 10 | 6.6 +/− 2.7 | 2x | 55.5 +/− 8.6 |
| 20 | 15.7 +/− 9.2 | 2–3x | 47.9 +/− 7.0 |
| 30 | 13.8 +/− 1.7 | 2–3x | 44.4 +/− 3.7 |
| 60 | 38.9 +/− 2.9 | 3x | 48.4 +/− 1.3 |
| 120 | 47.3 +/− 3.6 | >5x | 47.7 +/− 2.2 |

*mean +/− SEM, n = 3
**relative to pollen grain diameter

As seen in Table 5, a measurable increase in germination was detected with an exposure time as short as 10 minutes (Table 2). An exposure time between 1 to 2 hours was required for maximal germination frequency and tube length.

In vivo Fertility Rescue

The ability to restore self fertility to the CMF petunia by supplying the flavonol aglycone to the pollen at the time of pollination was tested by scoring for successful fertilizations resulting from self crosses of the CMF petunia done in the presence of added flavonols. Prior to self pollinating, flavonol aglycones were applied either (i) directly to the stigma or (ii) mixed with the freshly collected pollen. The most successful technique, measured by the quantity of seed set, required application of the flavonol to the stigma 12–16 hours prior to self pollination. 47 self crosses were performed with added kaempferol or quercetin, and nearly 60% (27 out of 47) produced seed pods. The number of seeds per pod varied from 31 to 287, and in germination tests >90% of the seeds in any single pod were viable. All self crosses done without added flavonols (>30 trials) yielded no seed set. The dominant CMF trait exhibited by the flavonoid-deficient petunia is tightly linked to a second dominant gene conferring kanamycin resistance (KAN) (Napoli, C., Lemieux, C. and Jorgensen, R., 1990, "Introduction to a Chimeric Chalcone Synthase Gene Into Petunia Results in Reversible Co-repression of Homologous Genes in Trans," *Plant Cell* 2:279–289). The KAN marker was used to test for segregation of the CMF character in the seeds produced by self crossing the flavonoid-deficient plants in the presence of added flavonol. Freshly harvested seeds were surface sterilized in 20% bleach, washed with sterile water and soaked for 30 min in 100 ppm GA3 solution before plating on germination plates (1×MS, 3 mM MES [pH 5.6], 1×B5 vitamin mix, 3% sucrose and 0.2% solidifying agent) containing 100 mg/ml kanamycin. After growth at 23° C. supplemented with a 16/8 hour photoperiod, resistance to kanamycin was scored by screening by seedlings sensitive to kanamycin. In the following Table 6, P-value represents the observed level of significance for a one degree of freedom chi-square goodness-of-fit test.

TABLE 6

| | | Seedlings | | |
|---|---|---|---|---|
| Pod | Total | KAN | KAN | P(3:1) |
| 1 | 75 | 58 | 17 | 0.74 |
| 2 | 65 | 50 | 15 | 0.83 |
| 3 | 81 | 59 | 22 | 0.75 |

Seeds germinated in the presence of 100 mg/ml kanamycin segregated in a 3:1 ratio of KAN resistance: sensitive as expected for a heterozygous dominant trait, as shown in Table 5.

Field Trial

A field trial was performed using a naturally occurring flavonoid-deficient maize mutant, white pollen, defective in flavonoid activity, which produces white, non-functional pollen, and is self sterile (E. H. Coe, S. M. McCormick, S. A. Modena, 1981, *J. Hered.* 72:318). A total of 45 self crosses were performed in the presence of added flavonoids and all of them (100%) produced fully filled ears while self crosses (45 trials) done without added flavonoids showed seed set less than 1% of normal. The maize white pollen plants used had stable recessive mutations at C2 and Whp introgressed into a W23 inbred background. The white pollen plants (c2/c2 whp/whp) were maintained by crossing with pollen from isogenic plants carrying a single functional copy of CHS (C2/c2 whp/whp). The plants were male sterile in self and sibling crosses and produced no visible flavonoid pigments in any tissues, including pollen and seeds. Standard genetic field practices were employed to insure that no contaminating pollen reached the silks of the white pollen plants. In addition, the white pollen block was surrounded with a pigmented kernel variety so that any contaminating kernels would immediately be recognized. Mutant white pollen from 50–100 plants was collected from the tassel bags, pooled, and divided into 2 portions. One portion was used "as is" for crosses and the other was mixed in an approximate 20:1 ratio with dry flavonoids (either quercetin, kaempferol, or a 50:50 mixture of the two). Prepared white pollen silks were pollinated with either the untreated or the flavonoid-supplemented white pollen and bagged immediately. The mature ears were harvested 45 days after pollination. White pollen crosses usually set ~200 kernels per ear and this number was routinely obtained in the biochemically complemented self-crosses. A total of 45 self crosses were performed in the presence of added flavonols and all of them (100%) produced fully filled ears while self crosses (45 trials) done without added flavonols showed seed set less than 1% of normal.

The foregoing confirm that flavonoids are required for pollen function as follows: (i) methanol and aqueous extracts of wild type stigmas and pollen can fully restore germination and tube growth to flavonoid-deficient pollen; (ii) these extracts contain the same flavonols that show activity in the in vitro fertility rescue assay described herein; (iii) the ability to rescue pollen germination and restore full tube growth in vitro and full seed in vivo is restricted to a specific class of flavonoid, the flavonol aglycones; (iv) the effective concentration of flavonol varies with structural features, but several compounds show a pronounced effect at levels less than 10 mM, well within physiological concentrations of these compounds. Flavonoids are produced by virtually all classes of plants from liverworts, mosses, and ferns to gymnosperms and angiosperms. Past flavonoid surveys often used dried leaf or root tissue from herbarium specimens; consequently, we do not have a good indication of how widespread is the occurrence of pollen flavonoids. Their ubiquitous presence in plant tissues and the fact that flavonoids have been identified in pollen extracts from several widely divergent species, would argue that flavonoids are a universal constituent of pollen. Most plant flavonols occur at the 3-0-glycosylated species (J. B. Harborne and C. A. Williams, 1988, in The Flavonoids, Advances in Research Since 1980 J. B. Harborne, Eds. (Chapman and Hail, London) chaps. 7, 8), and this is the predominant form in petunia pollen (O. Ceska and E. D. Styles, 1984, Phytochemistry 23:1822). Only the aglycone form can rescue pollen function which suggests that either low non-detected levels of the aglycone are normally present, or glycosidase activity is required to produce the aglycones that are necessary for fertilization.

Pollen provides the natural access point to manipulate the fertilization process. The loss of flavonoid expression resulting in CMF plants acts as a natural gametostat and not a gametocide. Full male function can be restored by external application of flavonols to the flavonoid-deficient pollen. This demonstrates identification of a factor involved in higher plant fertilization, and which can be used in a reversible male sterile system for the production of hybrid seed.

By connecting a gene affecting flavonol production to an inducible promoter, in accordance with the invention described herein, sterility may be controlled. One such gene already known involves the CHS genus, c2 and Whp described by Coe, et al., supra, incorporated herein by reference. Alternatively, the F3H gene may be isolated by generating a hybridization probe using PCR oligonucleotide primers (see Saiki, R. K., 1990, supra based on the published Antirrhinum F3H sequence.

Thus, by using a gene which controls production of flavonols as herein described, one can control sterility.

In general, in accordance with the invention described herein, a gene regulating flavonol production can be incorporated into the plant along with a necessary promoter which is inducible. The plant will be sterile since the critical flavonol is not produced, and when the promoter is induced, the plant will be fertile. The native gene producing flavonol is a normally fertile plant which may be inactivated by any of a variety of methods described below, such as backcrossing or homologous recombination.

INDUCIBLE PROMOTERS

In the practice of this invention the promoter region is removed from a cloned gene responsible for male fertility and is replaced with a promoter that only responds to a specific external stimulus. Thus, the gene will not be transcribed except in response to the external stimulus. As long as the gene is not being transcribed, its gene product—which is necessary for completion of pollen development—is not produced. This causes a breakdown in one or more of the biochemical/physiologic pathways of pollen development, which results in male sterility. The plant can only become fertile under the specific stimulus that activates the selected promoter.

An example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Wiegand, et al., "Messenger RNA Encoding a Glutathione-S-Transferase Responsible for Herbicide Tolerance in Maize is Induced in Response to Safener Treatment", *Plant Molecular Biology* 7: 235–243, 1986). It has been discovered that treating maize seed with GSTs increases the tolerance of the maize to the herbicides. Studies have shown that the GSTs are directly involved in causing this enhanced tolerance. This action is primarily mediated through a specific 1.1 kb mRNA transcription product. In short, maize has a naturally occurring quiescent gene already present that can respond to GSTs and that can be induced to produce a gene product. This gene has already been identified and cloned. Thus, in one embodiment of this invention, the promoter is removed from the GST responsive gene and attached to the male fertility gene that previously has had its native promoter removed. This engineered gene is the combination of a promoter that responds to an external chemical stimulus and a gene responsible for successful development of fertile pollen.

GENE INTRODUCTION

Several methods are known in the art for transferring cloned DNA into maize. These include electroporation-facilitated DNA uptake by maize protoplasts (Rhodes et al., "Genetically Transformed Maize Plants from Protoplasts", *Science*, Vol. 240 (Apr. 8, 1988); treatment of maize protoplasts with polyethylene glycol (Lyznik et al., "Stable Co-Transformation of Maize Protoplasts with Gus A and Neo Genes", *Plant Molecular Biology* 13: 151–161, 1989); and bombardment of maize cells with DNA laden microprojectiles (Klein, et al., "Genetic Transformation of Maize Cells by Particle Bombardment", *Plant Physiol.* (1989) 91, 440–444) and Klein, et al., "Factors Influencing Gene Delivery into *Zea Mays* Cells by High-Velocity Microprojectiles", *Bio/Technology* Vol. 6, May 1988).

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPTII). This gene conveys resistance to kanamycin, a compound that can be added directly to the growth media on which the cells grow. Plant cells are normally susceptible to kanamycin and, as a result, die. The presence of the NPTII gene overcomes the effects of the kanamycin and each cell with this gene remains viable. Another selectable marker gene which can be employed in the practice of this invention is the gene which confers resistance to the herbicide glufosinate (Basta®). A screenable gene commonly used is the b-glucuronidase gene (GUS). The presence of this gene is characterized using a histochemical reaction in which a sample of putatively transformed cells is treated with a GUS assay solution. After an appropriate incubation, the cells containing the GUS gene turn blue. Another screenable gene is a transcriptional activator for anthocyanin biosynthesis, as described in Bowen, et al., "R Genes as visual markers for corn transformation" Abstract edit. Gallagher, Academic Press (Oct. 1989); Ludwig, et al., "A regulatory gene as a novel visible marker for maize transformation" *Science* 247: 449–450 (Jan. 26, 1990). This gene causes the synthesis of the pigment anthocyanin. Cells transformed with a plasmid containing this gene turn red. Preferably, the plasmid will contain both selectable and screenable marker genes.

The plasmid containing one or more of these genes is introduced into either maize protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

INACTIVATION OF NATIVE GENE

It will be readily appreciated by those skilled in the art that a wide variety of methods are known to disable the native gene. Homologous recombination is but one of the methods known to those skilled in the art for rendering a native gene inoperative. Thus, when the engineered gene is homologously recombined into the plant, the native gene will be rendered inoperative. A good overview of this general process is provided by Yoder, J. I., and Kmic, Eric, in "Progress Towards Gene Targeting in Plants", *Genetic Engineering*, Vol. 13 (Plenum Press, New York, 1991). At page 265 of this reference, the authors note "gene targeting can be used to silence or replace the endogenous gene with an engineered allele; thus the phenotype of the altered gene, or its regulatory sequences, can be evaluated in planta." It is pointed out that genetic recombination takes place through breakage and reunion of DNA and the rejoining mechanism pairs the complimentary DNA sequences. (See, e.g. 271, supra).

A further discussion of intrachromosomal homologous recombination in plants is discussed at Peterhans, A., Schlupmann, H., Basse, C. and Paszkowski, J., "Intrachromosomal Recombination in Plants", *The EMBO Journal*, Vol. 9, No. 11, pp. 3437–3445, 1990.

A variety of different means, in addition to these specific examples, would be available to one skilled in the art. Mutations of the native gene can inactivate the gene. A still further example includes backcrossing, using generally accepted plant breeding techniques, to in effect "delete" the native gene. This replaces the native gene with the mutant. Backcrossing is often used in plant breeding to transfer a specific desirable trait from one inbred or source to an inbred that lacks that trait. This can be accomplished for example by first crossing an inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred. A result of any backcrossing method is that the "native" gene is replaced by the desired gene.

A unique method is discussed in the 1991 Science magazine, reporting on prior work relating to using "transgenic scissors". This article describes a method in which scientists may remove a marker gene which is attached to a gene having a desired trait in a plant. The "scissor," according to this method, is an enzyme obtained from a bacterial virus known as "Cre" for control of recombination. *Science*, p. 1457, Dec. 6, 1991. The enzyme is capable of snipping out any DNA located between a pair of 34-base pair sequences, called lox, for locus of crossing over. This is described in further detail in the patent application filed by Du Pont, and published at WO 91109957.

STERILITY SELECTION AND FERTILITY RESTORATION

After the gene is introduced into a plant, the appropriate plant types are selected, that is plants that are sterile. These plants are sterile because the isolated and cloned fertility gene does not have its native promoter and, therefore, is not producing its gene product that is crucial to successful pollen development. Therefore, the engineered gene acts as a recessive mutant allele of that gene. In normal plant biotechnology, once the desired genotype is identified following transformation and regeneration, the plants are selfed to recover that genotype. However, in the practice of this invention, the desired genotype cannot be selfed at the first generation because it is sterile. To obtain progeny, fertility must be induced by spraying the plants with a compound which induces transcription of the gene by activating the altered promoter. In the case of the GST promoters, the compound is preferably a GST-inducing compound such as N,N-diallyl-2-2-dichloroacetanide. The promoter attached to the fertility gene responds to this chemical and causes the transcription of the gene to begin. Once this occurs, the normal gene product is produced from the gene and some level of fertility is induced.

Once the initial isolation and propagation of the desired genotype is completed, the procedure is more straightforward. Only inbreds that are used as female parents in hybrid crosses are transformed into male sterile variants. Once they are transformed, the amount of male sterile/female fertile seed must be increased. This is accomplished by planting in an isolated area (away from other maize pollen) and spraying with a chemical to which the promoter responds. Spraying induces the promoter to start transcription of the gene attached to it. This will produce some degree of fertility.

A particular advantage of this system in comparison to systems such as that disclosed in PCT publication WO89/10396 of Mariani et al (based on Intl. Appl. No. PCT/EP89/00495), in which male sterility is induced, is that the treatment does not have to be 100% effective, because normally much more pollen is produced by a maize plant than is actually needed for fertilization of all available silks. Therefore, even low male fertility restoration will be effective in obtaining acceptable levels of seed increase. At the same time, self-pollination does not occur in hybrid seed production because the plants of this invention are normally male sterile and must be treated to become fertile.

Obviously, there are variations on this invention evident to one skilled in the art. The sterility system described herein can likewise be applied to control of a female fertility gene. The procedures are the same: identify a gene critical to female fertility, clone it, link an inducible promoter to the cloned gene, introduce it into the plant and silence the native DNA. The plant is then constitutively female sterile.

While the foregoing illustrates the preferred embodiment of the invention, it will be appreciated that various changes can be made without departing from the spirit and scope of the invention.

We claim:

1. A nucleotide sequence comprising a genomic DNA of about 1.4 kb, having at least two introns of about 100 to 130 bp in length, and which upon processing yield the cDNA of sequence ID no. 1 or the nucleotide sequence encoding the amino acid of sequence ID no. 2.

2. A plant having the nucleotide sequence of claim 1.

3. Plant cells having the nucleotide sequence of claim 1.

4. Plant parts of the plant of claim 2.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 1419 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

```
GAATTCGGCA CGAGGTCCAC CAGCATGGAG GAGAAGAGGA AGCTGCAGTG GCGGCGAGGG      60

CGTGATGGCA TCGTGCAGTA CCCTCACCTG TTCTTCGCGG CCCTGGCCCT GGCCCTCCTA     120

GTCGCGGACC CGTTCGGCCT CAGTCCGCTG GCCGAGGTCG ACTACCGGCC GGTGAAGCAC     180

GAGCTCGCGC CGTACGGGGA GGTCATGGGC AGCTGGCCCA GAGACAATGC CAGCCGGCTC     240
```

-continued

```
AGGCGCGGGA GGCTGGAGTT CGTCGGCGAG GTGTTCGGGC GGAGTCCAT  CGAGTTCGAT      300

CTCCAGGGCC GCGGGCCGTA CGCCGGCCTC GCCGACGGCC GCGTCGTGCG GTGGATGGGC      360

GAGGAGGCCG GGTGGGAGAC GTTCGCCGTC ATGAATCCTG ACTGGTCAGA AGAAGTCTGT      420

GCCAATGGAG TGAACTCAAC GACGAGGAAG CAGCACGAGA AGGAGGAGTT CTGCGGCCGG      480

CCGCTCGGCC TGAGGTTCCA CGGGGAGACC GGCGAGCTCT ACGTCGCCGA CGCGTACTAC      540

GGTCTCATGG TCGTTGGCCA GAGCGGCGGC GTGGCGTCCT CCGTCGCGAG GGAAGCCGAC      600

GGGGACCCCA TCCGGTTCGC GAACGACCTC GATGTGCACA GGAATGGATC CGTATTCTTC      660

ACTGACACGA GCATGAGATA CAGCAGAAAG GACCATCTGA ACATCCTGTT AGAAGGAGAA      720

GGCACCGGGA GGCTGCTCAG GTACGATCCA GAAACAAGTG CTGTCCATGT CGTGCTCAAG      780

GGACTGGTGT TCCCAAACGG CGTGCAGATC TCAGAAGACC ATCAGTTTCT TCTCTTCTCC      840

GAGACAACAA ACTGCAGGAT AATGAGGTAC TGGCTGGAAG GCCCAAGAGC GAGCGAGGTA      900

GAGGTGTTCG CGAACCTGCC GGGCTTCCCC GACAACGTGC GCTCCAACGG CAGGGGCCAG      960

TTCTGGGTGG CGATCGACTG CTGCCGGACG CCAGCGCAGG AGGTGTTCGC CAAGAGGCCG     1020

TGGCTCCGGA CCCTGTACTT CAAGTTCCCG CTGTCGCTCA AGGTGCTCAC TTGGAAGGCC     1080

GCCAGGAGGA TGCACACGGT GCTCGCGCTC CTCGACGGCG AAGGGCGCGT CGTGGAGGTG     1140

CTCGAGGACC GGGGCCACGA GGTGATGAAG CTGGTGAGCG AGGTGCGGGA GGTGGGCAGC     1200

AAGCTGTGGA TCGGAACCGT GGCGCACAAC CACATCGCCA CCATCCCCTA CCCTTTAGAG     1260

GACTAACCAT GATCTATGCT GTTTCAATGC CTCCTAATCT GTGTACGTCT ATAAATGTCT     1320

AATGCAGTCA CTGGTTGTAA TCTTGTTTGT GTTTGGCAAA TTGGCATAAT AATGGACAGA     1380

TTCAATGGGC AAAAAAAAAA AAAAAAAAAA AAACTCGAG                            1419
```

(2) INFORMATION FOR SEQ ID NO: 2:

(i) SEQUENCE CHARACTERISTICS:
        (A) LENGTH: 473 amino acids
        (B) TYPE: amino acid
        (D) TOPOLOGY: linear (xi) SEQUENCE DESCRIPTION: SEQ ID NO: 2:

```
Glu Phe Gly Thr Arg Ser Thr Ser Met Glu Glu Lys Arg Lys Leu Gln
 1               5                  10                  15

Trp Arg Arg Gly Arg Asp Gly Ile Val Gln Tyr Pro His Leu Phe Phe
                20                  25                  30

Ala Ala Leu Ala Leu Ala Leu Leu Val Ala Asp Pro Phe Gly Leu Ser
            35                  40                  45

Pro Leu Ala Glu Val Asp Tyr Arg Pro Val Lys His Glu Leu Ala Pro
    50                  55                  60

Tyr Gly Glu Val Met Gly Ser Trp Pro Arg Asp Asn Ala Ser Arg Leu
65                  70                  75                  80

Arg Arg Gly Arg Leu Glu Phe Val Gly Glu Val Phe Gly Pro Glu Ser
                85                  90                  95

Ile Glu Phe Asp Leu Gln Gly Arg Gly Pro Tyr Ala Gly Leu Ala Asp
                100                 105                 110

Gly Arg Val Val Arg Trp Met Gly Glu Glu Ala Gly Trp Glu Thr Phe
            115                 120                 125

Ala Val Met Asn Pro Asp Trp Ser Glu Glu Val Cys Ala Asn Gly Val
    130                 135                 140

Asn Ser Thr Thr Arg Lys Gln His Glu Lys Glu Glu Phe Cys Gly Arg
145                 150                 155                 160
```

```
Pro Leu Gly Leu Arg Phe His Gly Glu Thr Gly Leu Tyr Val Ala
                165                 170                 175

Asp Ala Tyr Tyr Gly Leu Met Val Val Gly Gln Ser Gly Gly Val Ala
            180                 185                 190

Ser Ser Val Ala Arg Glu Ala Asp Gly Asp Pro Ile Arg Phe Ala Asn
        195                 200                 205

Asp Leu Asp Val His Arg Asn Gly Ser Val Phe Phe Thr Asp Thr Ser
    210                 215                 220

Met Arg Tyr Ser Arg Lys Asp His Leu Asn Ile Leu Leu Glu Gly Glu
225                 230                 235                 240

Gly Thr Gly Arg Leu Leu Arg Tyr Asp Pro Glu Thr Ser Ala Val His
                245                 250                 255

Val Val Leu Lys Gly Leu Val Phe Pro Asn Gly Val Gln Ile Ser Glu
                260                 265                 270

Asp His Gln Phe Leu Leu Phe Ser Glu Thr Thr Asn Cys Arg Ile Met
            275                 280                 285

Arg Tyr Trp Leu Glu Gly Pro Arg Ala Ser Glu Val Glu Val Phe Ala
            290                 295                 300

Asn Leu Pro Gly Phe Pro Asp Asn Val Arg Ser Asn Gly Arg Gly Gln
305                 310                 315                 320

Phe Trp Val Ala Ile Asp Cys Cys Arg Thr Pro Ala Gln Glu Val Phe
                325                 330                 335

Ala Lys Arg Pro Trp Leu Arg Thr Leu Tyr Phe Lys Phe Pro Leu Ser
            340                 345                 350

Leu Lys Val Leu Thr Trp Lys Ala Ala Arg Arg Met His Thr Val Leu
            355                 360                 365

Ala Leu Leu Asp Gly Glu Gly Arg Val Val Glu Val Leu Glu Asp Arg
        370                 375                 380

Gly His Glu Val Met Lys Leu Val Ser Glu Val Arg Glu Val Gly Ser
385                 390                 395                 400

Lys Leu Trp Ile Gly Thr Val Ala His Asn His Ile Ala Thr Ile Pro
                405                 410                 415

Tyr Pro Leu Glu Asp Xaa Pro Xaa Ser Met Leu Phe Gln Cys Leu Leu
            420                 425                 430

Ile Cys Val Arg Leu Xaa Met Ser Asn Ala Val Thr Gly Cys Asn Leu
        435                 440                 445

Val Cys Val Trp Gln Ile Gly Ile Ile Met Asp Arg Phe Asn Gly Gln
    450                 455                 460

Lys Lys Lys Lys Lys Lys Leu Glu
465                 470

(2) INFORMATION FOR SEQ ID NO: 3:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (xi) SEQUENCE DESCRIPTION: SEQ ID NO: 3:

GCCCTGGCCC TGGCCCTCCT AGTCGCGGTC GCGACCCGTT CGGCCTC                47

(2) INFORMATION FOR SEQ ID NO: 4:

(i) SEQUENCE CHARACTERISTICS:
        (A) LENGTH: 16 amino acids
```

```
            (B) TYPE: amino acid
            (D) TOPOLOGY: linear (xi) SEQUENCE DESCRIPTION: SEQ ID NO: 4:

Ala Leu Ala Leu Ala Leu Leu Val Ala Val Ala Asp Pro Phe Gly Leu
1               5                   10                  15

(2) INFORMATION FOR SEQ ID NO: 5:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (xi) SEQUENCE DESCRIPTION: SEQ ID NO: 5:

GCCCTGGCCC TGGCCCTCCT AGTCGCGACC CGTTCGGCCT C                          41

(2) INFORMATION FOR SEQ ID NO: 6:

(i) SEQUENCE CHARACTERISTICS:
            (A) LENGTH: 14 amino acids
            (B) TYPE: amino acid
            (D) TOPOLOGY: linear (xi) SEQUENCE DESCRIPTION: SEQ ID NO: 6:

Ala Leu Ala Leu Ala Leu Leu Val Ala Asp Pro Phe Gly Leu
1               5                   10

(2) INFORMATION FOR SEQ ID NO: 7:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO: 7:

GATAGAATTC GGTACGGGAT TTTCCCATCC TACTT                                 35

(2) INFORMATION FOR SEQ ID NO: 8:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 8:

GGTAGAATTC GTTTTCGTTT CCGTCCCGCA AGTT                                  34
```